United States Patent
Ehbets et al.

(10) Patent No.: US 7,671,992 B2
(45) Date of Patent: Mar. 2, 2010

(54) MEASUREMENT SYSTEM AND SCANNING DEVICE FOR THE PHOTOELECTRIC MEASUREMENT OF A MEASUREMENT OBJECT PIXEL BY PIXEL

(75) Inventors: Peter Ehbets, Zürich (CH); Adrian Kohlbrenner, Thalwil (CH); Beat Frick, Buchs (CH)

(73) Assignee: X-Rite Europe GmbH, Regensdorf (CH)

( * ) Notice: Subject to any disclaimer, the term of this patent is extended or adjusted under 35 U.S.C. 154(b) by 427 days.

(21) Appl. No.: 11/666,365

(22) PCT Filed: Oct. 28, 2005

(86) PCT No.: PCT/EP2005/011592
§ 371 (c)(1),
(2), (4) Date: Apr. 26, 2007

(87) PCT Pub. No.: WO2006/045621
PCT Pub. Date: May 4, 2006

(65) Prior Publication Data
US 2009/0091760 A1 Apr. 9, 2009

(51) Int. Cl.
*G01J 3/46* (2006.01)
*G01N 21/25* (2006.01)

(52) U.S. Cl. ................ 356/416; 356/402; 356/407; 358/497

(58) Field of Classification Search ........... 356/402, 356/407, 409, 411, 419, 420, 425, 416; 358/497, 358/473, 484; 235/462.45, 472.01
See application file for complete search history.

(56) References Cited

U.S. PATENT DOCUMENTS

| | | | |
|---|---|---|---|
| 4,449,147 A | 5/1984 | Ogasawara | |
| 4,575,249 A | 3/1986 | Grieger | |
| 5,963,333 A * | 10/1999 | Walowit et al. | 356/425 |
| 6,028,682 A | 2/2000 | Ott et al. | |
| 6,262,804 B1 * | 7/2001 | Friend et al. | 356/402 |
| 6,535,279 B1 | 3/2003 | Lampersberger et al. | |
| 6,597,454 B1 | 7/2003 | Berg et al. | |
| 7,391,543 B2 * | 6/2008 | Ohara | 358/483 |
| 7,443,506 B2 * | 10/2008 | He et al. | 356/402 |
| 2002/0191188 A1 * | 12/2002 | Hubble et al. | 356/402 |

OTHER PUBLICATIONS

PCT International Search Report dated Jul. 2, 2006.

* cited by examiner

*Primary Examiner*—L. G Lauchman
(74) *Attorney, Agent, or Firm*—McCarter & English, LLP

(57) ABSTRACT

The measuring device comprises a lighting system, a photoelectric receiver unit and optical means. The lighting system applies light to image elements disposed in strip-shaped lighting regions (15) at a standardized angle of incidence range. The photoelectric receiver unit comprises several photoelectric line sensors (21) disposed parallel at a distance apart which are sensitized to different wavelength ranges by color filters (22) connected upstream. The optical means comprise linear optical arrays (31) which pick up the measurement light reflected by the image elements at a standardized range of angle of reflection and direct it to one of the respective line sensors (21). By means of optical screening and other structural features, cross-talk effects between adjacent image elements are largely reduced.

33 Claims, 13 Drawing Sheets

Fig. 3
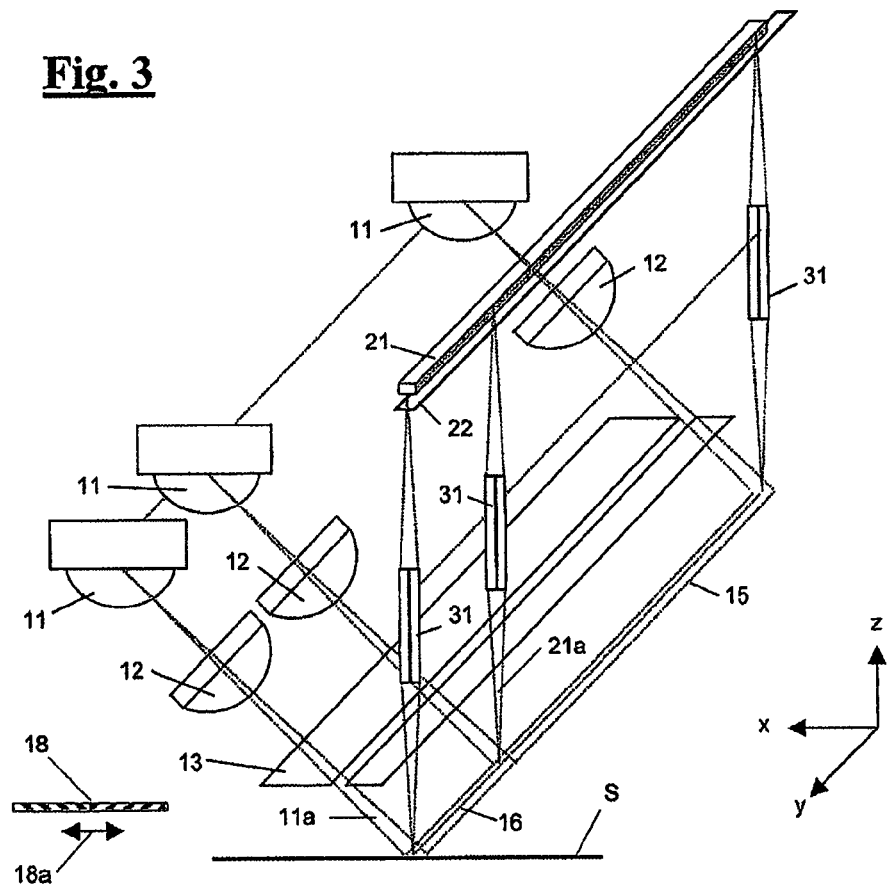
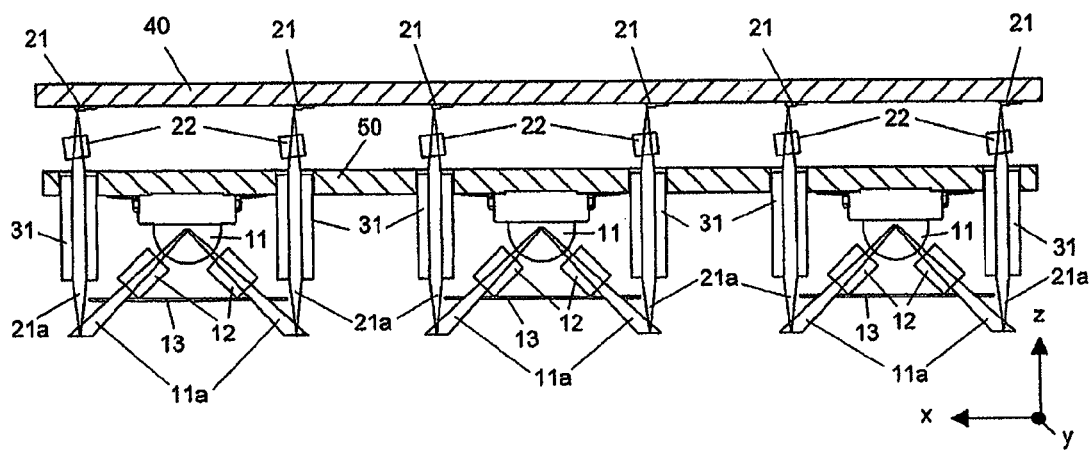
Fig. 7

Fig. 13
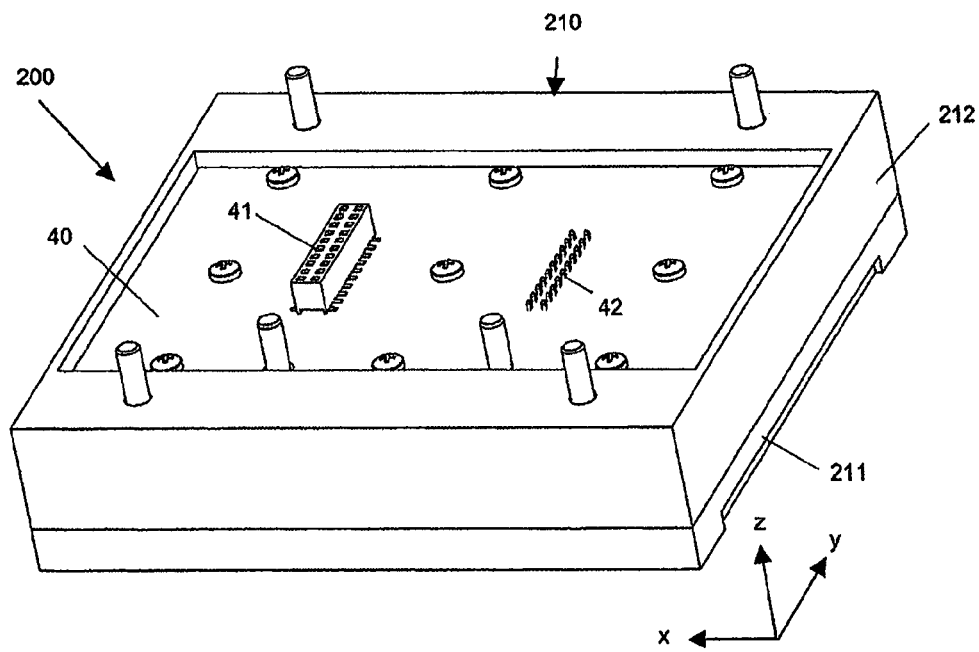
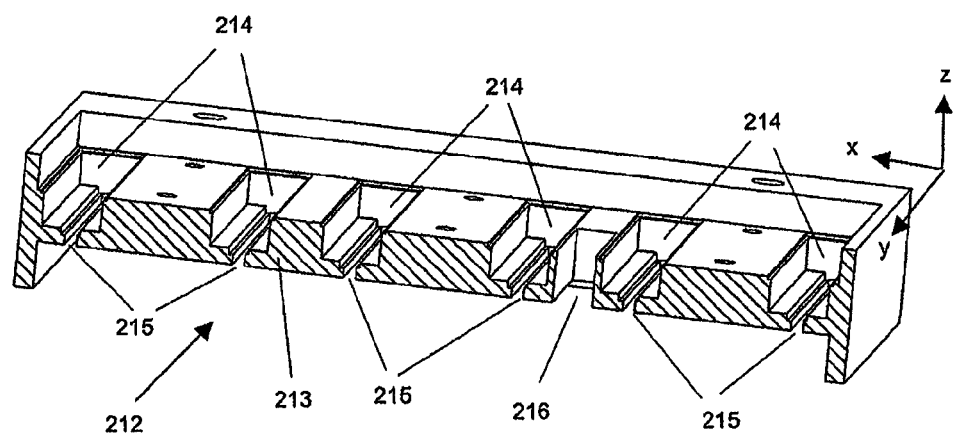
Fig. 14

Fig. 20
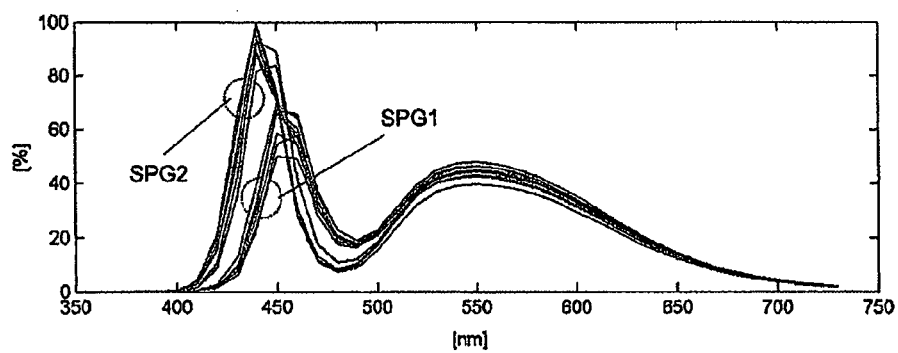
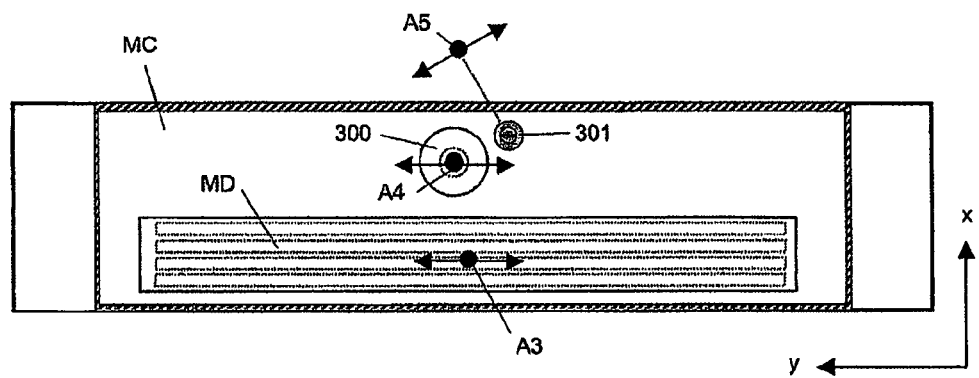
Fig. 21

MEASUREMENT SYSTEM AND SCANNING DEVICE FOR THE PHOTOELECTRIC MEASUREMENT OF A MEASUREMENT OBJECT PIXEL BY PIXEL

BACKGROUND OF THE INVENTION

The invention relates to a measuring device for photoelectrically measuring a measurement object on the basis of image elements, in particular a printed sheet preferably printed in multiple colors, of the type outlined in the introductory part of independent claim 1. The invention further relates to a scanning device equipped with such a measuring device in the form of a measuring table of the type outlined in the introductory part of independent claim 29.

BACKGROUND OF THE INVENTION

Measuring systems and scanning devices of this type are generally known as scanners. They are used in the graphics industry as a means of quality control and for controlling printing processes, for example.

A first known type of scanner has an individual measuring head, which can be moved in one or in two dimensions relative to the measurement object—as a rule a printed sheet. In the situation where the measuring head can be moved in one dimension, the measurement object can be moved in the other dimension. The measuring head respectively scans a small region of the measurement object, what is referred to as an image element or pixel, photoelectrically and each image element is individually scanned by individually moving the measuring head or the measurement object accordingly. The scanning operation may be performed on a densitometric, colorometric or spectral basis, whereby appropriate measurement signals are generated which are then available for processing and/or evaluation. A major disadvantage of these known scanners is the large amount of time involved in scanning a printed sheet of standard size completely, due to the fact of having to move individually the image elements to be measured, which makes them unsuitable for use as a means of automatically controlling or regulating modern printing machines as a rule.

A second known type of conventional scanner is described in patent specification U.S. Pat. No. 6,028,682 (≈DE-A 196 50 223) for example. Scanners of this generic type are equipped with a measurement carriage, which extends transversely across a measuring table in one dimension and can be moved across the second dimension driven by a motor. Disposed in the measuring carriage is a longitudinally extending measuring beam, which contains a large number of measuring heads disposed in a straight line. As the measuring carriage is moved across the measuring table, each measuring head scans the measurement object along a separate scanning track. The measuring heads are provided in the form of pure illuminating and pick-up units and each is connected via an optical multiplexer to a light source and a spectrometer in a time sequence. Although these known scanners are significantly faster than scanners with an individual measuring head mentioned above and are also suitable for applications requiring colorimetric control of a printing process, they are still nevertheless relatively slow on the one hand and mechanically or optically extremely complex on the other hand.

On the basis of the prior art known from patent specification U.S. Pat. No. 6,028,682 (≈DE-A 196 50 223), the objective of this invention is to improve a measuring device and a scanning device of the generic type in terms of scanning speed and design complexity, whilst simultaneously preserving its suitability for quality control purposes in the graphics industry and for colorimetrically controlling printing processes.

As a means of detecting images, i.e. for digitizing documents and similar physical forms, scanners equipped with line scanners are known, which are capable of photoelectrically measuring the respective image elements of a whole image line in one pass. Depending on the design, either the line scanner is moved across the stationary form or the form is moved transversely to the stationary line scanner in order to digitize the entire form line by line. The line scanner comprises a linear light source which is able to illuminate an entire image line simultaneously and a linear sensor array comprising a large number of individual sensors to which the light reflected from the measurement object is directed by what is likewise a linear-shaped optical array. The maximum spatial resolution is theoretically determined by the size of the individual sensors but in practice is reduced to a greater or lesser degree by the effect of scattered light and cross-talk. Color separation takes place either on the basis of a time sequence using either several differently colored light sources (mostly red, blue, green) to illuminate the image lines or a light source which can be switched to different colors, or alternatively an essentially white illuminating light is used with several rows of sensors disposed in parallel, each of which receives light of different wavelength ranges (red, blue, green), which can be set up using upstream filters, for example. Light-emitting diodes (LED) or fluorescent lamps are often used as light sources. Two different systems are commonly used for the arrays of sensors. In the case of the first system, the so-called Contact Image Sensor (CIS), the image lines are imaged by means of gradient index lenses (known as Selfoc Arrays) aligned in rows on a 1:1 scale on the optoelectronic detector rows, and the detector rows comprise optoelectronic line detectors seamlessly aligned in rows (e.g. photodiode arrays). This being the case, the length of the detector rows is identical to the length of the image lines to be scanned. In the case of the second system, the image lines are imaged onto the detector rows by means of a lens and a reducing optical system is often chosen for this purpose, for example imaging on a scale of 1:4. This specifically makes it possible for the length of the detector rows to be smaller than the length of the image lines. If the reduction is sufficient, this makes it possible to set the detector rows up using a single optoelectronic line detector (with a large number of individual sensors) rather than a group of them.

The known scanners of this latter type are very fast and are generally totally satisfactory in terms of image detection. However, if the image elements of the measurement object have to be colorimetrically measured to a high degree of precision, as is generally vital in applications involving quality control and for controlling printing processes, such scanners are not suitable. This is due on the one hand to the cross-talk effects which occur between the individual image elements with scanners of this type and on the other hand to the fact that these scanners are not designed for genuine color measurement processes. When it comes to obtaining correct color and density measurement values, an important aspect is conforming to the measurement geometry prescribed in the relevant standard (typically 45°/0°, e.g. DIN 165361, Part 2), which determines the angle of illumination and reception and permits only a small aperture angle (typically <=5°, e.g. DIN 165361, Part 2). Neither of the commercially available image scanners of these types (CIS and optical imaging system) satisfies these geometric measuring conditions.

SUMMARY OF THE INVENTION

The present invention provides a measuring device for photoelectrically measuring a measurement object on the basis of image elements, in particular a printed sheet preferably printed in multiple colors, which measuring device simultaneously photoelectrically scans a plurality of image elements of a measurement object disposed in a line and generates associated measurement signals for every scanned image element, with a lighting system for applying illuminating light to the image element of the measurement object, with a wavelength range-selective photoelectric receiver unit and with optical pick-up means which pick up the measurement light reflected by the illuminated image elements of the measurement object and direct it to the photoelectric receiver unit, and the photoelectric receiver unit converts the measurement light directed to it from the image elements of the measurement object into corresponding measurement signals for the image elements of the measurement object, wherein the lighting system has several parallel linear-shaped arrays of light-emitting diodes which apply illuminating light to the measurement object in a number of parallel illuminating strips, and the lighting system has means for limiting the angle of incidence range so that essentially every image element disposed in the illuminating strip and illuminated receives light at an angle of incidence range standardized for color measuring applications, and the photoelectric receiver unit has a number of parallel photoelectric line sensors disposed at a distance apart corresponding to the number of illuminating strips which are oriented parallel with the longitudinal extension of the illuminating strips and are sensitized to different wavelength ranges by color filters connected upstream, and the optical pick-up means has a number of linear optical arrays corresponding to the number of line sensors which are each oriented parallel with the illuminating strips and direct measurement light reflected from an image line within the illuminating strips onto one of the respective line sensors, and the linear optical arrays are configured so that the measurement light from essentially every image element of the image lines is picked up at only an angle of reflection range for standard color measuring applications, and the illuminating strips with the associated linear optical arrays and line sensors are optically screened from one another so that measurement signals from image lines in adjacent illuminating strips can not mutually affect one another.

Furthermore, the present invention provides a scanning device for photoelectrically measuring a measurement object on the basis of image elements, in particular a printed sheet preferably printed in multiple colors, with a measuring table to which the measurement object can be secured for the measurement, with a measuring device which can be moved above the surface of the measuring table which simultaneously photoelectrically scans a plurality of image elements respectively lying in a line of the measurement object secured to the measuring table and generates an associated measurement signal for every scanned image element, with a drive system which moves the measuring device above the measurement object so that all the image elements of the measurement object can be detected, with a measurement and drive control system for the measuring device and the drive system and with a processing unit for processing and evaluating the measurement signals scanned by the measuring device from the scanned image elements of the measurement object, and the measuring device is equipped with a lighting system for applying illuminating light to the image elements of the measurement object, with a wavelength range-selective photoelectric receiver unit and with pick-up means, which pick-up means pick up measurement light reflected by illuminated image elements of the measurement objects and direct it to the photoelectric receiver unit, and the photoelectric receiver unit converts the measurement light from the image elements of the measurement object directed to it into corresponding measurement signals for the image elements of the measurement object, wherein the lighting system comprises several parallel linear arrays of light-emitting diodes which apply illuminating light to the measurement object in parallel illuminating strips, and the lighting system has means for limiting the angle of incidence range so that essentially every image element disposed in the illuminating strips and illuminated receives light only at an angle of incidence range standardized for color measuring applications, and the photoelectric receiver unit comprises a number of parallel photoelectric line sensors corresponding to the number of illuminating strips which are oriented parallel with the longitudinal extension of the illuminating strips and are sensitized to different wavelength ranges by color filters connected upstream, and the optical pick-up means comprise a number of linear optical arrays corresponding to the number of line sensors which are oriented parallel with the illuminating strips and direct measurement light reflected from a respective image line within the illuminating strips onto a respective one of the line sensors, and the linear optical arrays are configured so that the measurement light from essentially every image element of the image lines is picked up only at an angle of reflection range standardized for color measuring applications, and the illuminating strips with the associated linear optical arrays and line sensors are optically mutually screened off from one another so that measurement signals from image lines in adjacent illuminating strips can not mutually affect one another.

The expression "for color measurement applications of standardized incident or reflecting angle ranges" used below should be understood as meaning the standardized measurement geometry and associated angle ranges stipulated in the above-mentioned standards.

BRIEF DESCRIPTION OF THE DRAWINGS

The invention will be explained in more detail with reference to the appended drawings. Of these:

FIG. 3 is a diagram illustrating the basic structure of the measuring device proposed by the invention disposed in the measuring carriage, FIG. 7 is an operating diagram illustrating an example of a preferred embodiment of the measuring device proposed by the invention disposed in the measuring carriage, FIG. 13 illustrates a measuring module from outside, viewed at an angle, FIG. 14 shows a cut-away view of the top part of the housing of the measuring module illustrated in FIG. 12, viewed from an angle, FIG. 20 shows typical emission spectra of white light-emitting diodes, FIG. 21 illustrates an example of an embodiment of the scanning device proposed by the invention with an additional spectral measuring head.

SUMMARY OF THE INVENTION

Figure 2:
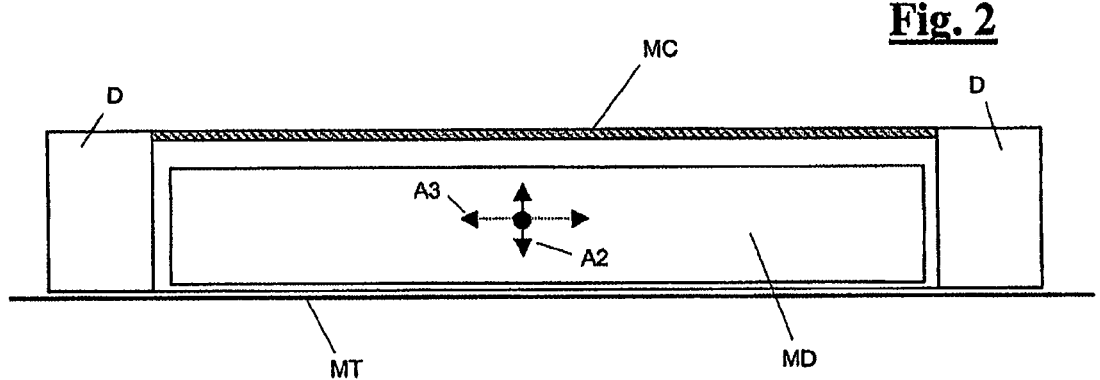
FIG. 2 shows a view in partial longitudinal section parallel with the y-z co-ordinate plane through the measuring carriage of the scanning device.

In terms of its general structure, the scanning device proposed by the invention corresponds to standard measuring apparatus of the type commonly used in the graphics industry as a means of photoelectrically measuring pixels picked up from a printed sheet during a printing process. The scanning device comprises a sub-structure in the form of a measuring table MT with a rectangular surface which is usually inclined, on which the measurement object S—printed sheet to be measured—can be positioned. The printed sheet S typically contains several (in this instance four, for example) graphic images P1-P4 and one (or more) color-measuring strips CMS. In order to position the measurement object S, the measuring table MT is provided with stops, although these are not illustrated. The measurement object S is preferably secured on the measuring table MT by electrostatic means or by means of suction mechanisms. Disposed on the measuring table MT is an elongate measuring carriage MC, on or in which a measuring device MD (FIG. 2) is disposed. The measuring carriage MC extends across the depth of the measuring table MT in the direction of the y co-ordinate and can be moved linearly backwards and forwards across its width in the direction of co-ordinate x by motor, for which purpose appropriate drive and control units are provided on the measuring carriage MC and on or underneath the measuring table MT. The drive system is only symbolically indicated by reference D in the drawing and the movement of the measuring carriage MC in the x direction is indicated by arrow A1. Inside the measuring carriage MC is the actual measuring device MD which can be raised and lowered by means of conventional drive mechanisms, not illustrated, in the direction of the z co-ordinate axis relative to the measuring table surface and, in specific variants, also in the direction of the y co-ordinate axis (to a limited degree). These two movement options are indicated by arrows A2 and A3 in FIG. 2.

Disposed on the measuring table MT parallel with the measuring carriage MC is a white reference WR. It is used to calibrate the measuring device MD. The calibration process is usually run by the measuring device MD, which measures the white reference, prior to every measuring operation. The white reference was measured beforehand (usually at the factory) with the aid of an external device and the measurement values stored in the memory of the scanning device, as a rule in the computer C. Such a calibration process is standard practice with spectral photometers and as such is prior art, although for the purpose of the invention, it is also run (in the y direction) depending on location, as will be explained in more detail below.

The scanning device also has a processing unit in the form of an external computer C with a keyboard K and a color monitor M. The computer C operates in conjunction with a measurement and drive control system MDC (FIG. 9) disposed on the measuring table MT or in the measuring carriage MC and processes the measurement signals generated by the measuring device MD disposed in the measuring carriage MC and forwarded to it via the measurement and drive control system MDC and, amongst other things, is able to display the image data of the scanned measurement object S on the monitor M. Via the measurement and drive control system MDC, the computer C is also able to command and control the movements of the measuring carriage MC and the measuring device MD disposed in it. To this extent, the scanning device corresponds to the systems known from the prior art, such as the devices commercially available from Heidelberger Druckmaschinen AG or those specified in patent specification U.S. Pat. No. 6,028,682 (corresponding to DE-A-196 50 223), for example. The mechanical design and the motorized movements of the measuring carriage MC and measuring device MD are described in detail in U.S. Pat. No. 6,028,682 and the skilled person therefore requires no further explanation in this respect. It goes without saying that the measuring carriage MC may also be disposed parallel with the x co-ordinate direction, in which case all other orientations and directions of movement would likewise be rotated by 90°.

FIG. 3 illustrates the main structure of the measuring device MD proposed by the invention disposed in the measuring carriage MC. As a whole, the measuring device constitutes a multi-channel line scanner (with regard to wavelength ranges), although only the elements relating to one color channel (wavelength range) are illustrated in FIG. 3 to provide a clearer overall illustration. A full measuring device MD with several color channels is illustrated in FIG. 7, for example, and will be explained in more detail below.

The measuring device MD constitutes the core of the invention and, as such, may also be used in conjunction with other scanning devices or simply on its own. The measuring device MD proposed by the invention may also be fitted on a printing machine, for example, thereby enabling printed sheets to be measured in-line during or immediately after printing whilst the printing machine is running.

The most important components of the measuring device MD are a lighting system for applying illuminating light to the measurement object, optical pick-up means for receiving the measurement light reflected from the measurement object and a wavelength range selective reception system for converting the reflected measurement light into electric measurement signals.

Figure 4:
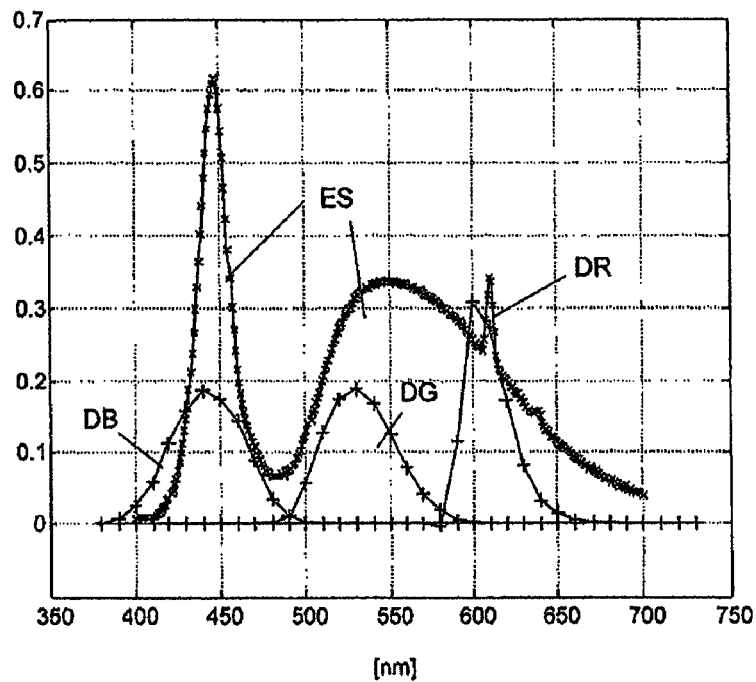
FIG. 4 illustrates a typical spectrum of a white LED light source.

For each color channel or, in one particularly advantageous embodiment of the invention, for every two physically adjacent color channels, the lighting system has a greater number of light sources 11 in the form of light-emitting diodes, which are linearly aligned in a row in the y direction. For each light source 11, it preferably also has a (cylindrical) collimator lens 12 as well as a continuous slot diaphragm 13 extending in the longitudinal direction parallel with the y co-ordinate. The light sources 11 apply illuminating light to the measurement object S within an illuminating strip 15 extending in the longitudinal direction parallel with the y co-ordinate and at least across a part of the measurement object S. The disposition is such that illuminating light is directed onto every image element of the measurement object S to be scanned lying within the illuminating strip 15 at a defined angle of incidence (typically 45°/0°, e.g. DIN 165361, Part 2) appropriate for measuring color. This is achieved by the collimator lenses 12 and the slot diaphragm 13. The collimator lenses 12 create a virtually parallel optical path. The focal distance of the lenses is selected so that the divergence angle of the collimated optical path (in the y direction) is smaller than 5-10°. This implementation permits a largely uniform continuous linear illumination. The optical path of the illumination is indicated by reference 11a in FIG. 3. The slot diaphragm 13 limits the angle of incidence transversely to the longitudinal extension of the illuminating strip, in other words in the direction of the x axis. The light-emitting diodes 11 used may be of the "white" illuminating Luxeon DS 25 type sold by Lumileds Lighting LLC, San Jose, Calif., USA, for example. The typical emission spectrum (spectral radiant power) ES of such light-emitting diodes is given in the diagram of FIG. 4t. By way of comparison, the bandpass characteristics DB, DG, DR of so-called status E filters are also given in the diagram.

The photoelectric receiver unit comprises (for each color channel) a line sensor 21 and a color filter 22 connected upstream, which sensitizes the line sensor to its wavelength bandpass range. The line sensor comprises one or more so-called CIS elements (contact image sensor), each of which in turn has a large number of individual light sensors integrated in a straight line on a chip. A suitable CIS element is that of the PI6045J type sold by Peripheral Imaging Corporation, San Jose, Calif., USA with a resolution of 600 dpi, for example.

Figure 5:
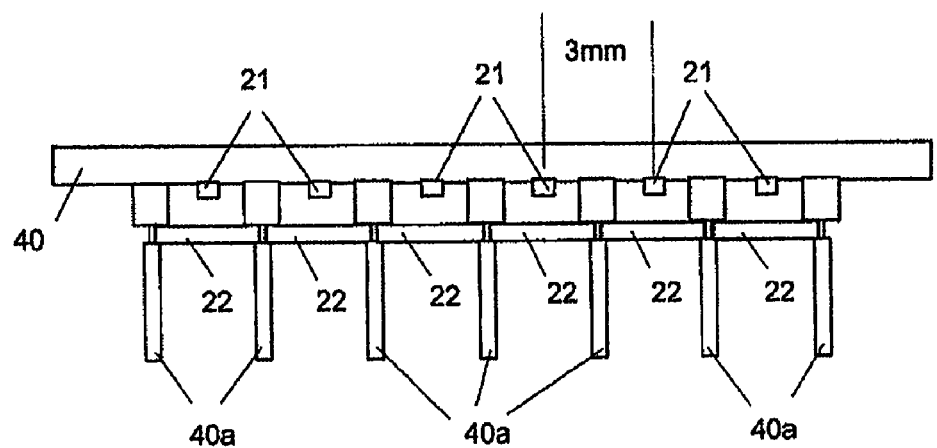
FIG. 5 is a detailed diagram illustrating the way in which rows of sensors used in the measuring device are mounted.

FIG. 5 is a schematic diagram illustrating how line sensors 21 (in this instance six, for example) are mounted on a common circuit board 40 at a mutual distance of what is usually approximately 3 mm. Dividing walls 40a secured on the circuit board are used on the one hand as mounts for the color filters 22 and on the other hand as a means of optically separating the optical paths. The dividing walls 40a may also be disposed directly up to the outlet surface of the Selfoc lens arrays 31 which will be described in more detail below. This enables an optimum optical separation of the different color channels (wavelength measurement channels) to be achieved.

Alternatively, the color filters 22 may be adhered directly to the line sensors 21 or, with the aid of spacers, to the circuit board 40. The individual spaces can then be optically isolated by means of the dividing walls or black casting compound. Another option is to adhere the filters directly or using spacers onto the front or rear face of the optical pick-up system or to secure them by some other known method. Another mounting option for the color filters 22 is to fit them in a frame-type filter holder, for example, and fixedly secure this filter holder in position.

Figure 6:
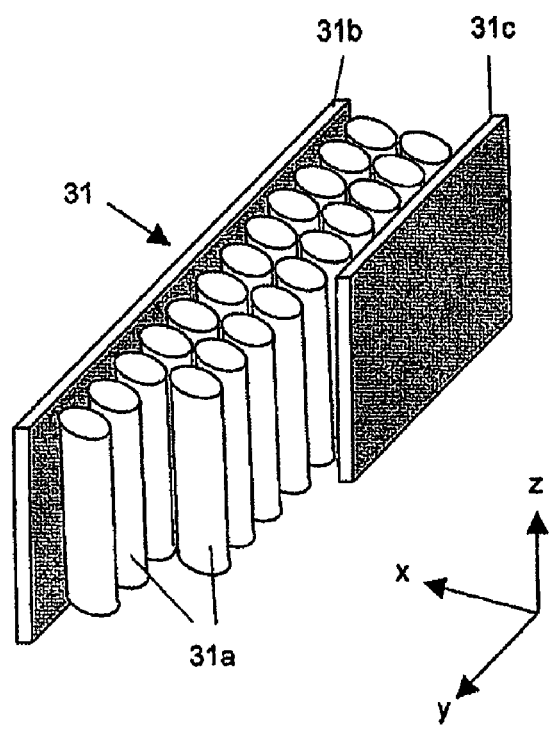
FIG. 6 is a detailed diagram illustrating the structure of so-called Selfoc arrays used in the measuring device.

The optical pick-up means comprise (for each color channel) a linear optical array 31, which is preferably configured as an essentially linear array of gradient index lenses, so-called Selfoc lens arrays. Like the line sensor 21, the linear optical array 31 extends parallel with the y co-ordinate direction. A typical layout of a Selfoc lens array 31 is illustrated in FIG. 6. Here, there are two rows of gradient index lenses 31a between two outer walls 31b and 31c and the gaps between the lens fibers and the walls are cast with an opaque plastic. Suitable Selfoc lens arrays are sold by the NSG company.

The linear optical array 31 directs the reflected measurement light applied to the image elements of the measurement object S by the illuminating light onto the co-operating line sensor 21 (measurement light optical path 21a). The optical array 31 is configured and disposed so that it receives the measurement light reflected by every scanned image element within a defined angle of incidence range suitable for color measurements (typically 0°+/−5°, e.g. DIN 165361, Part 2). The scanned image element line (per color channel) is denoted by reference 16 in FIG. 3.

In practice, it is important to position the slot diaphragm 13 in the optical path of the light as close as possible to the measurement object S. The slot diaphragm 13 limits the illuminated surface on the measurement object. It typically has an aperture width of 1 mm or less. The illuminated surface of the measurement object (illuminating strip 15) therefore has a width (in the x direction) which is shorter than the field of vision of the optical array or Selfoc lens array 31 (in the x direction). This improves suppression of scattered light and allows density measurements to be taken of small measurement fields with a high density in a white environment.

A basic problem of linear illumination is the fact that a point in the measurement field receives light from all the light sources (light-emitting diodes). This being the case, the light from light-emitting diodes offset from the row is no longer oriented at 45° but hits the measurement field at bigger angles. However, the bigger angles do not conform to the standardized color measuring geometry, which only permits an angle of illumination in the range of 40° to 50° (45°+/−5°). Deviations from the standard geometry give rise to measurement errors, which are caused by a different surface effect and by other absorption paths through the color layer.

Figure 15:
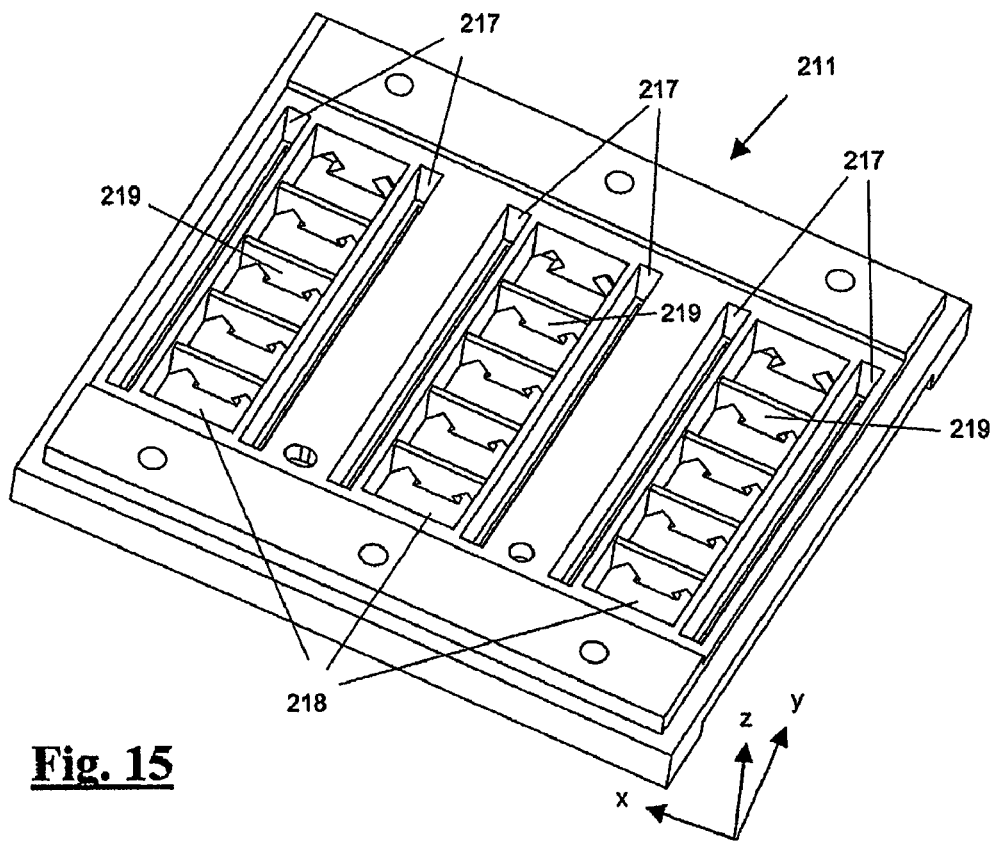
FIG. 15 illustrates the base plate of the measuring module illustrated in FIG. 12, viewed from an angle.
Figure 19:
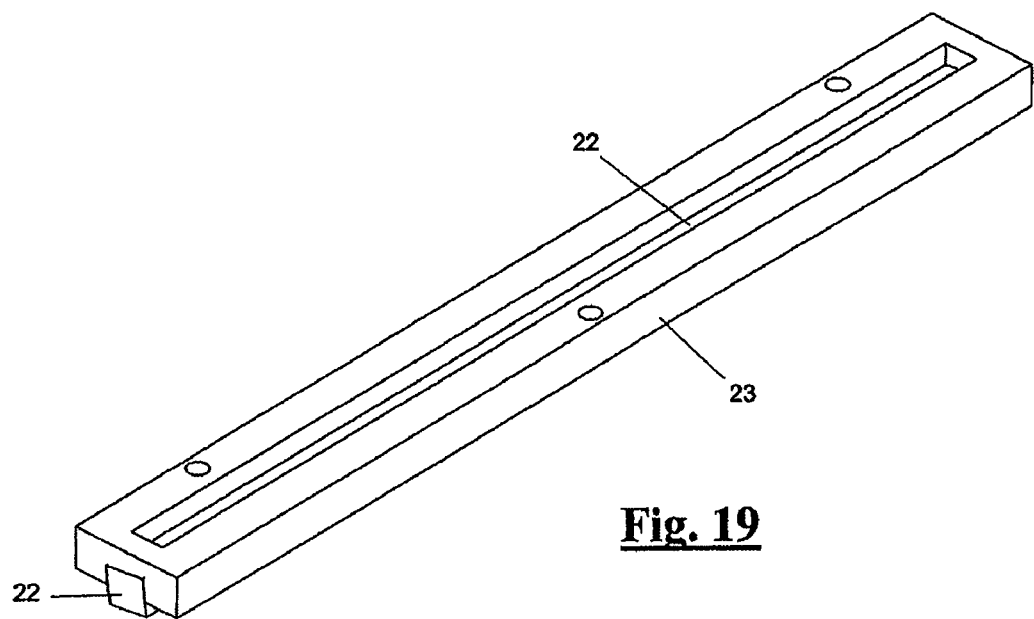
FIG. 19 is a view from an angle illustrating a filter holder with a color filter inserted in it.

The effective angle range for the illumination must therefore be limited. This can be done using a plate structure, for example, disposed between the individual light-emitting diodes of a row and the measurement field. In FIG. 15, such plates are indicated by reference 219, for example.

However, the plates should not be too big, otherwise a relatively large amount of light will be lost. Every measurement point sees only the light of a single LED in the permissible angle range.

By virtue of another important aspect of the invention, a better option for limiting the angle of illumination to conform the standard geometry is to use the collimator lenses 12 mentioned above, which are disposed along every light-emitting diode-row source and are preferably physically grouped in lens arrays (several lenses made from an integral plastic part). In the embodiment illustrated as an example in FIG. 18, the integral design of the collimator lenses 12 is clearly visible.

Every collimator lens 12 of a lens array collimates the light of mainly one light-emitting diode 11 (or, if using a lot of small light-emitting diode chips, of a spatially limited array of several light-emitting diode chips). The focal distances of the collimator lenses 12 are selected so that the divergence angle and the peripheral angle of the illumination of the measurement field in the longitudinal direction of the light-emitting diode row (y direction) are smaller than +/−10°. This produces an overlap within the illuminating strip 15 and results in a homogeneous distribution of lighting intensity. The screening plates 219 between the light-emitting diodes 11 mentioned above prevent light from a light-emitting diode reaching the measurement object via lenses of a neighboring light-emitting diode.

It is sufficient to use cylindrical lenses for the collimator lenses 12, which collimate the light beams in the longitudinal direction of the light-emitting diode row. The light-emitting diode row light source has a limited extension in the direction perpendicular to the row so that it satisfies the requirements stipulated for the standard geometry in this dimension, even without additional optics. Furthermore, the slot diaphragm 13 limits the width of the illuminating strip 15.

A measurement object, especially a printed sheet, must be measured without contact. The support surface for the sheet is not perfectly flat across the relatively large sheet surface as a rule. During scanning, this therefore results in variations in the distance between the measurement object and the measuring device. These must not be allowed to affect the measurement values. Accordingly, the lighting optics and measuring optics must not be dependent on distance beyond the tolerated range of a couple of tenths of a millimeter.

The lighting system illuminates beyond the visual field of the measuring optics (optical array 31) (the illuminating strip 15 is wider than the width of the scan line 16 detected by the optical array 31). Since the detection angle of the optical array 31 must be very limited (in accordance with the color measuring standards, detection angles of +/−5° only are tolerable), the light or beam density is measured by the optical array in the measurement field, which is not dependent on distance. The lighting system must therefore generate only a constant illumination intensity irrespective of the distance.

A concept whereby illumination can be applied at less than 45° irrespective of distance is already known and involves disposing a radiation source with a Lambert emission characteristic parallel with the plane of the measurement field. The position of the radiation source relative to the measurement field is selected so that the light hits the measurement field at an angle of 45°. In accordance with the photometric law, such lack of sensitivity to distance is achieved for a range of distance variations that is sufficient for the practical application. This concept, which is known per se, may be seen in FIG. 3 and may also be applied to this invention.

As mentioned above, in order to measure the measurement object in several color channels, the measuring device MD is equipped with several configurations illustrated in FIG. 3. These configurations (light sources 11, collimator lenses 12, slot diaphragm 13, line sensor 21, color filter 22, linear optical array 31) are disposed parallel with one another at a slight mutual distance apart (in the x direction) and differ solely due to different color filters 22.

FIG. 7 is a highly simplified diagram in section parallel with the x-z co-ordinate plane, illustrating the main structure of a measuring device MD equipped with six color channels. The longitudinal directions (y direction) of the linear arrays of light sources 11, the slot diaphragm 12, optical array 31, color filters 22 and the line sensors 21 extend perpendicular to the plane of the drawing. In this particularly advantageous embodiment of the invention, two respective (physically) adjacent color channels are split into a row of light sources 11 and a slot diaphragm 13. Accordingly, the slot diaphragms 13 are provided in the form of double slotted diaphragms, each with two slots. This symmetrical layout with a common lighting system for every two adjacent color channels is of advantage in many respects. Firstly, it is more cost-effective than providing a separate lighting system for every color channel. Secondly, the measuring ranges of the individual color channels are spatially better separated. This reduces the amount of scattered light and possible cross-talk between the color channels, thereby improving measuring performance. As may also be seen from FIG. 7, the line sensors 21 are mounted on a common line sensor circuit board 40 and the light sources 11 are mounted on a common light-emitting diode circuit board 50. Further details of the mechanical structure of the measuring device MD will be explained below. The lighting and measurement light optical paths are again indicated by references 11a respectively 21a.

As illustrated in FIG. 7, the linear optical arrays 31 and the line sensors 21 of the six color channels are offset from one another in the x direction. Consequently, each of the six line sensors 21 receives measurement light at a given instant from different image element lines 16 of the measured object S extending in the y direction. By moving the measuring carriage MC and hence the measuring device MD across the measurement object S in the x direction, however, measurement light from all the image element lines 16 of the measurement objects S is applied to all six line sensors 21 sequentially in time. If the measuring device MD is fitted on a printing machine, the relative movement between the measuring device and measurement object is obtained by feeding the printed sheet under the measuring device.

By contrast with image detection, the effects of cross-talk represent a major problem in colorimetric and densitometric applications. Special measures are therefore necessary to reduce the effects of this cross-talk as far as possible.

A first measure or a first means involves mutually screening off the optical paths of the measurement light for the individual color channels. This may be done by providing appropriate dividing walls between the individual linear optical arrays 31. In principle, these dividing walls may also extend to just short of the surface of the measurement object S, provided they do not shadow the light needed from the lighting system to illuminate the image elements. The dividing walls reduce cross-talk between the individual line sensors and color channels. Such dividing walls may also advantageously be mounted in the detector-side space between the optical arrays 31 and the sensors 21 and associated color filters 22. In the preferred embodiment of the measuring device illustrated in FIGS. 13-18, the dividing walls are formed by housing parts. Details may be seen in FIGS. 13-18 and the associated parts of the description.

Another way of damping cross-talk is to select the distances between the lighting rows and hence between the line sensors and Selfoc arrays so that they are big enough for directed surface reflex of a measuring line not to hit the opening of the Selfoc arrays of the adjacent color channels.

Another way of damping cross-talk is for the color filters 22 connected upstream of the line sensors 21 to be positioned at a slight angle and by angle in this respect is meant a rotation out of the x-y plane about the axial direction. This angled position reduces cross-talk in the longitudinal direction of the line sensors. This cross-talk damping measure may also be clearly seen in the preferred embodiment illustrated as an example in FIGS. 13-18.

An alternative option for damping cross-talk is to run an appropriate test sample, which is placed on the measuring table MT and moved or scanned by the measuring carriage MC and the measuring device MD. The test sample is typically positioned parallel with the white reference strip WR (FIG. 1) on the measuring table mentioned above. The cross-talk behavior of the measuring device MD can be characterized periodically during operation, preferably before each measurement sequence, by scanning the test sample. This characterization takes place along the measuring device MD, i.e. in the y direction, depending on position. Since the scattered light carrying the actual information measured by reference to a selected image element depends on both the location of the cross-talk behavior of the measuring device MD and on the image data of the adjacent image elements in terms of its intensity, it is preferable to make allowance for both when computing compensation of the cross-talk. In other words, the amount of scattered light of each individual image element is estimated on the basis of the image data of adjacent image elements and the characterization of the measuring device MD depending on location and then subtracted from the associated measurement value.

It goes without saying that with an increasing number of color channels (on line sensors sensitized to different wavelength ranges) and a simultaneously decreasing bandwidth of the wavelength ranges, the more precise the color measurement which can be obtained will be. With 14-16 color channels at a distance of 20 nm each, the spectral resolution is the same as that of conventional spectral measuring heads. However, with an increasing number of color channels, the complexity of the system is also more complex and the computing resources for processing the measurement values is also increased. Conversely, with too low a number of color channels, it is no longer possible to obtain a color measurement that is precise enough for the intended purpose. An optimum comprise as regards measuring accuracy and manufacturing costs in terms of one aspect of the invention is to provide 6-12 color channels in the visible range plus possibly one additional channel in the near infrared range.

Figure 8:
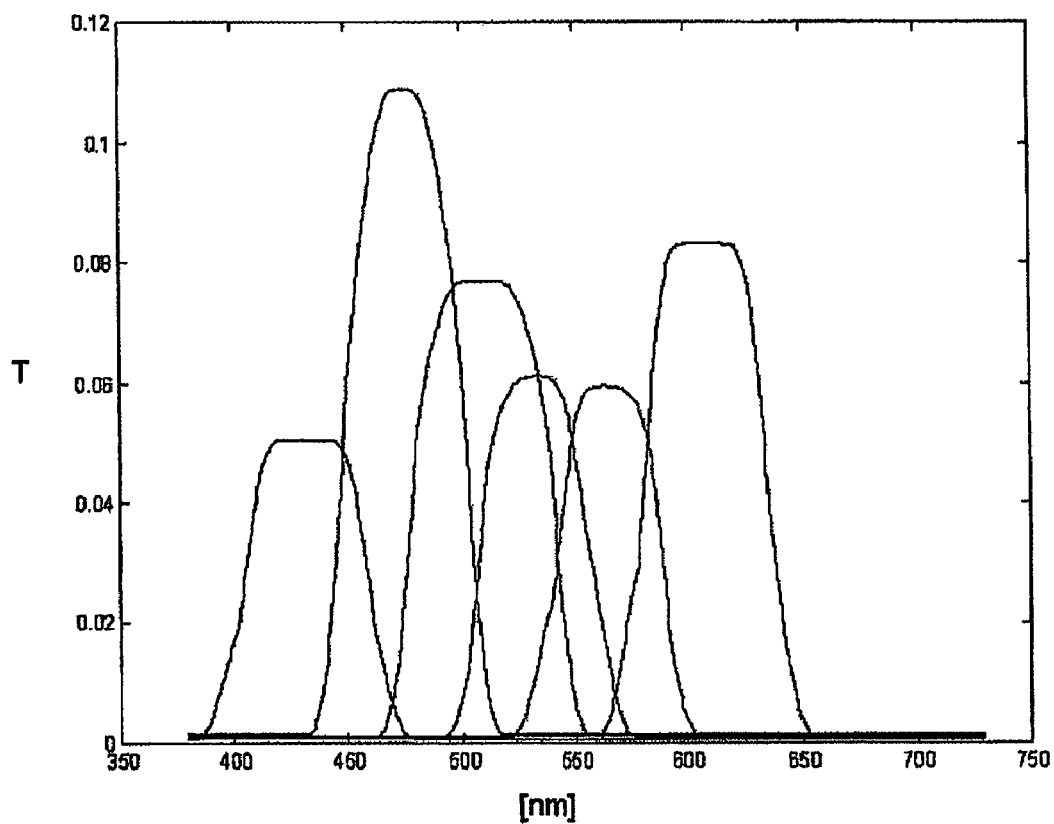
FIG. 8 shows bandpass curves of typical appropriate color filters.

In a preferred example of an embodiment, six color channels are provided for the visible range of the spectrum, in other words six line sensors each with a respective color filter connected upstream. This being the case, three of the six color filters preferably have the bandpass characteristics of the normalized color density filters for taking color density measurements and the other three color filters are optimised with a view to obtaining an accurate color measurement. The typical bandpass curves of these six color filters are given in the diagram of FIG. 8. They have bandpass characteristics and typical half-widths of 30 nm to 60 nm. After scanning, therefore, six scanning values are available for every image element of the measurement object, from which all other relevant data can be computed, for example in the external computer C. The color densities are directly available as scanning values in the three color channels equipped with the color density filters.

For some applications, it is also necessary to run a scan in the near infrared range. This being the case, the measuring device proposed by the invention may also be equipped with an infrared channel. An IR filter is connected upstream of one of the line sensors for this purpose. Since light-emitting diodes emitting white do not have a sufficient IR element as a rule, an additional IR light source must be provided for this situation in the form of a linear array of IR light-emitting diodes. Alternatively, a mixture of white and IR radiating light-emitting diodes may also be provided in the linear light-emitting diode arrays. Further explanation of this will be given below.

Figure 9:
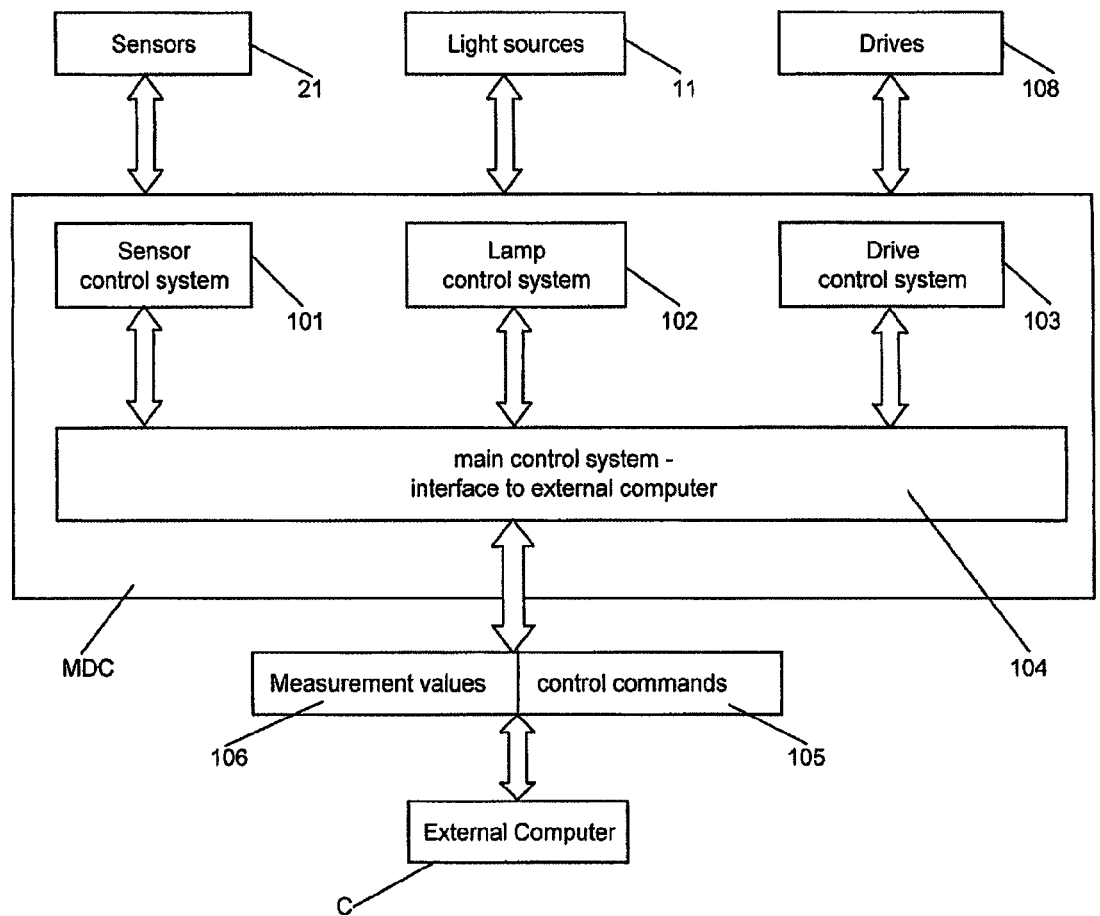
FIG. 9 is a block diagram illustrating the operating principle of the electronic measurement and control system of the scanning device.

FIG. 9 illustrates the measurement and drive control system MDC of the scanning device in the form of a rough block diagram. It comprises a sensor control system 101, a lamp control system 102 and a drive control system 103 as well as a main controller 104, which co-operates with the other three control systems and simultaneously also establishes the connection to the external computer C. The sensor control system 101 reads the measurement values from the line sensors 21, the lamp control system 102 controls the light sources 11 in the lighting unit and the drive control system 103 controls drive motors 108 for the movement of the measuring carriage MC and the measuring device MD disposed in it in three directions of motion x, y, and z. The main controller 104 co-ordinates and controls the other three control systems on a higher-ranking level and simultaneously establishes the connection to the external computer C. The main controller 104 receives control commands 105 from the external computer C and sends the (digitally supplied) measurement values 106 generated by the line sensors 21 to the external computer. In principle, the measurement and drive control system MDC is the same as commercially available scanner devices of this type in terms of its function, and the specific functions necessary for activating the line sensors 21 and light-emitting diodes 11 are specified directly in the data specifications of the manufacturers of these elements. The skilled person therefore requires no further explanation as to how the measurement and drive control system MDC is implemented.

In the examples of embodiments described above, the measuring device MD extends across the entire height (y direction) of the measurement object. Since printed sheets are usually relatively large, the length of the measuring device in the y direction and the length of the line sensors 21, color filters 22 and linear optical arrays 31 may easily be 80 cm and more. Manufacturing such long line sensors, color filters and optical arrays is technically very complex, however.

One possible way of getting round this problem is to select the length (in the y direction) of the measuring device MD so that it is basically shorter than the scanning region to be passed over in the y direction. In this case, the whole measurement object would have to be scanned in two or more scanning passes (movements of the measuring carriage MC and hence the measuring device MD in the x direction above the measurement object), and the measuring device MD in the measuring carriage MC would have to be moved in the y direction accordingly for every scanning pass.

By virtue of another aspect of the invention, however, this problem is preferably solved by building the measuring device MD in a modular design, in other words made up of a number of relatively short measuring modules in the y direction of an essentially identical design, each of which incorporates all elements of the measuring device and in their totality cover the scanning region to be passed over in the y direction. The measuring modules may be approximately 50 mm long (in the y direction) for example and the entire measuring device may comprise 16 modules, for example.

Figure 10:
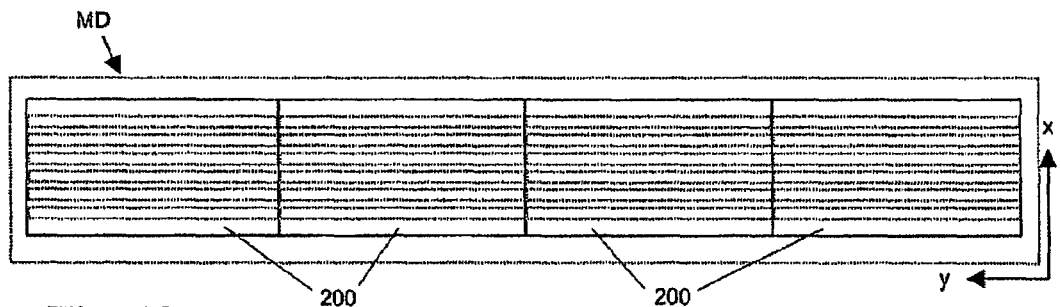
FIG. 10 is a diagram illustrating the operating principle of a first variant of a modular structure of the measuring device.
Figure 11:
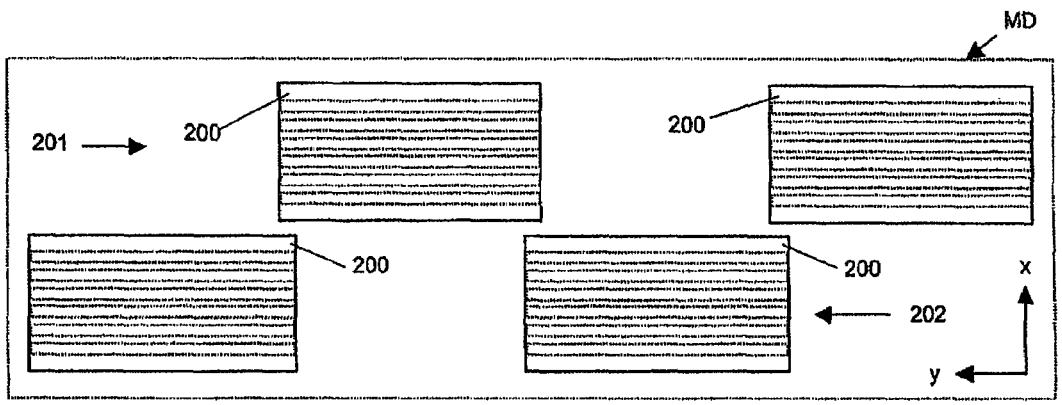
FIG. 11 is a diagram illustrating the operating principle of a second variant of a modular structure of the measuring device.

FIGS. 10 and 11 are schematic diagrams illustrating two variants of measuring device MD, which in this instance is made up of only four measuring modules. The hatched stripes inside the measuring modules symbolize the color channels of each module (of which there are again six, for example).

FIG. 10 illustrates the four measuring modules 200 of the measuring device MD placed seamlessly one adjacent to the other (in the y direction). However, obtaining a seamless alignment may be difficult from a technical point of view because slight scanning gaps might occur at the joining points. Consequently, in the preferred example illustrated in FIG. 11, the measuring modules 200 are split into two groups 201 and 202 which form two parallel straight rows in the x direction. The measuring modules 200 of the two groups 201 and 202 mutually sit on a gap and overlap slightly in the x direction. As a result of this overlap, scanning gaps are avoided and the requirements placed on the precision of the construction are less critical. However, this approach makes the control aspect more complex because the sensor rows of the measuring modules of the two groups respectively sit above one and the same image element line of the measurement object at different instants in time.

The individual measuring modules 200 of the measuring device MD are normally of an identical construction. However, by virtue of another aspect of the invention, it would also be possible to use measuring modules with different color channels in the measuring device MD in order to increase the total number of color channels. To this end, it is merely necessary to use different color filters. For example, in the embodiment illustrated in FIG. 10, each uneven measuring module 200 could incorporate six first color channels and each even measuring module 200 could incorporate six second color channels different from the first ones. Likewise, in the embodiment illustrated in FIG. 11, the measuring modules 200 of one group 201 could incorporate six first color channels and the measuring modules 200 of the other group 202 could incorporate six second color channels different from the first ones. The entire measuring device MD in both variants would then offer a color resolution of twelve color channels. In this case, two scanning passes would naturally be necessary to scan the measurement object completely and the measuring device MD would have to be moved in the y direction essentially by a module length.

Figure 12:
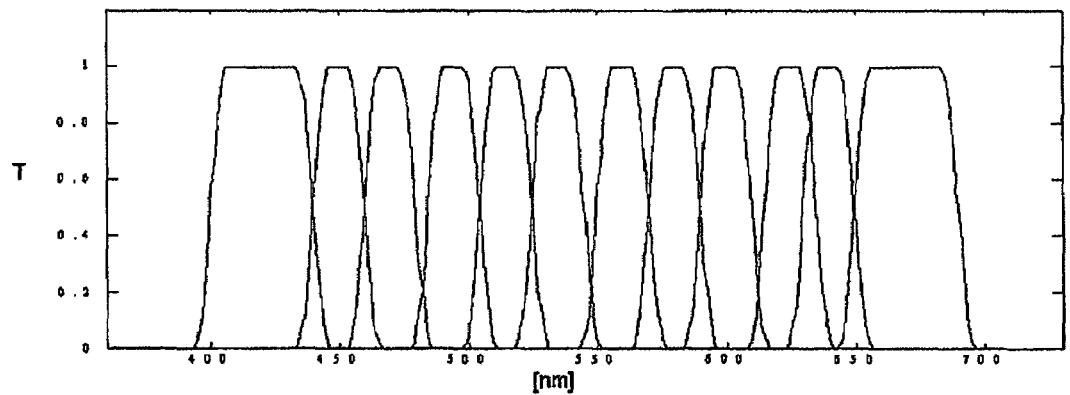
FIG. 12 illustrates other bandpass characteristics of typically used color filters.

FIG. 12 illustrates the spectral distribution of the measurement filters for the situation where 12 different color filters and color channels are provided. Here, 10 different color filters with 20 nm half-width are used in the relevant measurement range of 450 nm to 640 nm. This resolution corresponds to the requirements stipulated for spectral color measuring techniques in the standards (CIE15.3 or DIN 5033). In the peripheral regions, where normal observer functions are low, wider filters are selected because no strong color differences occur in these regions. Three color filters are specially selected for the density measurement, exactly in accordance with the ISO density standard Status I from standard ISO 5. The color filters are set out in the table below together with the center wavelength CWL and the half-width HW.

|  | 1 | 2 | 3 | 4 | 5 | 6 | 7 | 8 | 9 | 10 | 11 | 12 |
|---|---|---|---|---|---|---|---|---|---|---|---|---|
| CWl [nm] | 420 | 450 | 470 | 495 | 515 | 535 | 560 | 580 | 600 | 625 | 640 | 670 |
| HW [nm] | 40 | 20 | 20 | 20 | 20 | 20 | 20 | 20 | 20 | 20 | 20 | 40 |

This filter selection enables good measurement performance for the color and density measurement of printed samples with a reduced number of color filters, which is equivalent to a spectral measuring technique.

The filter selection and disposition for the measuring modules 200 may also be such that certain color channels (color filters) are provided in all the measuring modules. For example, a red, a green and a blue filter each may be provided in every measuring module 200, although these red, green and blue color filters are not identical but only spectrally as close to one another as possible. Six color channels per module will again then result in a total color resolution of the twelve color channels. This design of the color channel distribution enables the entire measurement object to be scanned with a single scanning movement (e.g. outward movement of the measuring carriage) in the color channels provided in all the measuring modules. These scanning values can then be used to display a preview image (which is not exactly 100% in terms of the color), for example.

The structure of a measuring module 200 again designed for 6 color channels, for example, will be described in more detail below with reference to FIGS. 13-19. It goes without saying that the measuring modules may also be designed for more or fewer color channels. The configuration of the described measuring module 200 corresponds to that illustrated in FIG. 7.

As may best be seen from the overall view illustrated in FIG. 13, the measuring module 200 has a housing 210 in which all the optical and electrical components are accommodated. The housing 210 is made from metal and simultaneously serves as a cooling element for dispelling heat. The two-part housing 210 essentially comprises a base plate 211 and a top part 212 connected to it.

Figure 16:
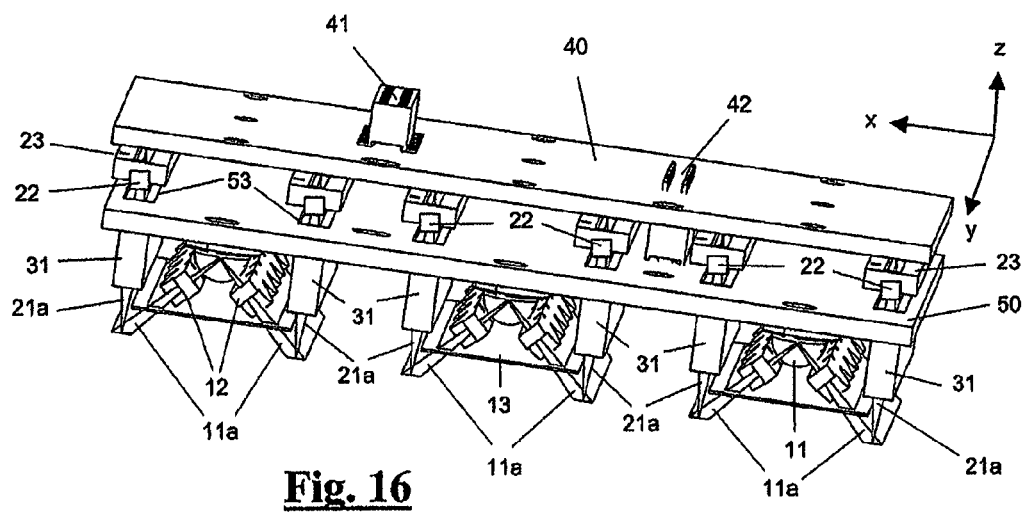
FIG. 16 is a view from an angle, illustrating the main components of the measuring module illustrated in FIG. 12 without the housing.
Figure 17:
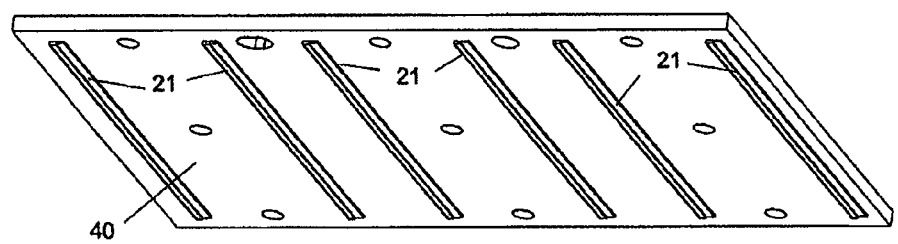
FIG. 17 is a view from an angle, illustrating a sensor circuit board with rows of sensors of the measuring module illustrated in FIG. 12 mounted on it.
Figure 18:
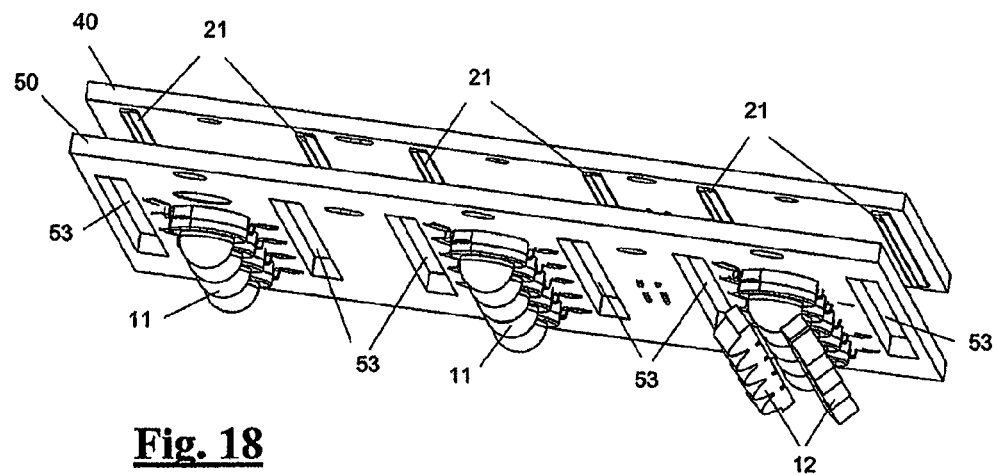
FIG. 18 is a view from an angle illustrating a light-emitting diode circuit board with light-emitting diodes of the measuring module illustrated in FIG. 12 mounted on it.

FIG. 16 provides an overall view of the functional elements of the measuring module 200 accommodated in the housing, including lighting and measurement optical paths 11a respectively 21a. As may be seen, there are two parallel circuit boards 40 and 50, on which all the electrical components are mounted. The line sensor circuit board 40 at the top in the drawing, which simultaneously closes the housing 210 at the top, bears on its bottom face (FIG. 17) six line sensors 21 of the design already described above (CIS elements). The line sensors 21 are disposed parallel and extend in the y direction. Disposed on the top face of the line sensor circuit board 40 is a plug-in connection 41, by means of which the measuring module 200 can be electrically connected to the measurement and drive control system MDC described in more detail above. Plug pins 42 are also illustrated, which are plugged into a socket 50 on the light-emitting diode circuit board 50 lying underneath, thereby establishing the electrical connection to the light-emitting diode circuit board 50. On the bottom face of the light-emitting diode circuit board 50, there are three parallel rows of light-emitting diodes 11 (five in each case in this instance) extending in the y direction mounted in good thermal contact (FIG. 18).

In FIG. 16, there are also six linear arrays of collimator lenses 12 extending in the y direction, three double-slotted diaphragms 13 extending in the y direction, six linear optical arrays 31 (Selfoc lens arrays) extending in the y direction and six color filters 22 accommodated in filter holders 23 extending in the y direction. The color filters 22 are slightly rotated about the y axis in order to reduce the effects of cross-talk—see the explanations of this given above. The collimator lenses 12 are fitted and secured in cavities of the base plate 211 of the housing 210. The linear optical arrays 31 are secured in slots 53 of the light-emitting diode circuit board 50 and likewise fit in appropriately shaped cavities of the base plate 211. The double-slotted diaphragms 13 are mounted on the bottom face of the base plate 211 of the housing 210. The frame-shaped filter holders 23 with the color filters 22 held in them are fitted and secured in cavities of the housing top part 212 of a matching shape.

As illustrated in FIG. 14, the housing top part 212 is of an essentially frame-shaped design and has a relatively thick intermediate wall 213, which is provided with six elongate cavities 214 extending in the y direction as well as six elongate slots 215, likewise extending in the y direction. The cavities 214 are used to accommodate the filter holders 23 with the color filters 22 fitted in them, illustrated in detail in FIG. 19. The slots 215 allow the optical paths 21*a* of the measuring light to pass between the linear optical arrays 31 and the line sensors 21. The line sensor circuit board 40 and the light-emitting diode circuit board 50 are mounted on or underneath the intermediate wall 213 (when the measuring module is in the assembled state). The light-emitting diode circuit board 50 is made from a good heat conductive material and dispels the heat generated by the light-emitting diodes into the housing 210. Another cavity 216 provides space for the socket 52 on the light-emitting diode circuit board 50.

The base plate 211 illustrated in FIG. 15 has six parallel slots 217 extending in the y direction and three elongate windows 218 extending in the y direction. The slots 217 allow the optical paths 21*a* of the measuring light reflected by the scanned lines of the measurement object to pass through to the linear optical arrays 31. The windows 218 provide space for said six rows of collimator lenses 12 and are closed at their bottom face towards the housing exterior by the three double slotted diaphragms 13 (not illustrated in FIG. 15). In order to reduce the effects of scattered light in the longitudinal direction (y direction), four screening plates are respectively disposed in the windows 218, each of which is fitted so that it lies between two light-emitting diodes 11.

Fitting the components of the measuring modules in cavities of the base plate 211 and the housing top part 212 provides a good optical separation of the individual color channels so that there can be no cross-talk effects between the individual color channels.

In the embodiment illustrated as an example in FIGS. 13-18, light source lines are used comprising 5 (per line) commercially available white high-power light-emitting diodes (LEDs), mounted on the light-emitting diode circuit board 50 in good thermal contact at a distance of 10 mm. The light-emitting diodes 11 used are white 1W LEDs fitted in normal housings using "surface mount" technology (SMT) with Lambert emission characteristics, from the manufacturer Lumileds. With five of these relatively large light-emitting diodes, a scanning line of 50 mm in length can be illuminated sufficiently uniformly. The double-slotted diaphragms 13 and the collimator lenses 12 ensure that the measurement object is illuminated in the region of the scanning strip detected by the measuring module in accordance with the standard (angle of incidence 45°+/−5°) and sufficiently homogeneously.

Instead of using fewer large light-emitting diodes, however, it is also possible to use a larger number of smaller light-emitting diodes, which are likewise disposed on the light-emitting diode circuit board 50. For example, it is possible to use 20 small low-power light-emitting diodes based on "chip on board" technology (COB) for every light source line. In particular, it is also possible to use many small low-power LEDs with COB technology, occupying a small space. So-called LED clusters may be formed. This will afford a light source equivalent to the high-power LED chips in terms of surface. In this disposition, it is also possible to use a combination of different LED types with different spectral emission wavelengths (see also the explanations given below).

In terms of practical implementation, it is of advantage if the line sensors 21 for all pick-up channels (six in this instance) are mounted on the common line sensor circuit board 40 at a constant distance from the measurement plane, as illustrated in the drawing. The Selfoc lens arrays used for the linear optical arrays 31 have chromatic aberrations, however, which means that the sharp image plane is shifted longitudinally (z direction) as a function of the wavelength. The typically used GRIN lens arrays of the SELFOC type made by Nippon Sheet Glass, Japan, have typical chromatic lengthways aberrations in the range of from 0.4 to 0.8 mm across the spectral operating range.

In order to solve this problem, the optical arrays or Selfoc lens arrays 31 are fitted slightly offset in the z direction so that the optimum operating distance for the wavelength of the pick-up channel can be obtained on the measurement object side. On the image side (line sensor side) of the Selfoc lens arrays 31, the optical path difference is compensated due to the fact that thicker color filters are used at the short wavelength than at the long wavelength. The requisite change in thickness is calculated using the known formula for the defocus by a plane parallel plate, as described in every reference work relating to optical technology.

For reasons of cost, it would be desirable to measure several spectral channels (wavelength ranges) using only one pick-up channel, in other words one and the same optical array (Selfoc lens array) 31 and one and the same line sensor 21. It would be of particular interest to combine the infrared range used for printing technology in the range of between 850 nm and 950 nm with the measurement of another wavelength range (color channel), for example with a center wavelength at 420 nm and half-width of 40 nm. There is no problem detecting these different wavelength ranges with the same sensor given the line sensors used because numerous commercially available silicon-based sensors have a perfectly good sensitivity in the range of 400 nm to 950 nm.

By virtue of another aspect of the invention, a combination is achieved whereby the measurement object is alternately illuminated with light from the two wavelength ranges to be combined and the measurements of the two wavelength ranges (color channels) are nested one in the other by a time division multiplexing process. The illuminating light is therefore adapted alternately to the one color channel (e.g. light of a blue LED) and to the other color channel (e.g. light of an IR LED). The prerequisite for this, naturally, is that the relevant light-emitting diode line is fitted with different light-emitting diodes with the requisite emission characteristics and the different light-emitting diodes can be selectively activated. This may in turn be done by the measuring and control device MDC mentioned above.

This alternating dual lighting system could theoretically be operated without additional filters. However, since precise densitometric and colorimetric measurements are needed for the applications addressed here and the light-emitting diodes never have a sharply defined illumination spectrum, the required bandpass characteristics must be obtained by optical bandpass filters. By virtue of another aspect of the invention, the color filter 22 assigned to the relevant line sensor 21 is provided in the form of a double bandpass filter for this purpose. Most ideally, such a double bandpass filter transmits for example between 400 nm-440 nm and 850 nm-950 nm and blocks in the remaining range of the spectrum in question (e.g. between 380 nm and 1000 nm). It would also be possible to use a double bandpass filter with the following characteristics: transmission below 440 nm and above 850 nm and blocking between 440 nm and 850 nm. The double bandpass filter is preferably provided in the form of a pure interference filter.

The spectrum of what is referred to as "phosphor-converted" white light-emitting diodes (e.g. light-emitting diodes sold by Lumileds, USA) is split into two parts: the shorter wave part which is induced directly by the LED semiconductor material and the longer wave part indirectly resulting from the phosphor. The light of the semiconductor, the so-called pump LED, is typically in the UV or deep blue part of the spectrum and of a relatively narrow band (typically narrower than 100 nm). The light element emitted by the phosphor extends from blue to red and is of a broader band (typically 100 nm to 200 nm). FIG. 20 illustrates typical emission spectra of such white LEDs.

Such light-emitting diodes are suitable as light sources for densitometric and colorimetric measuring devices and in particular for spectral photometers in principle. However, they are problematic from several points of view, the two most important of which are as follows. A spectral hole usually occurs between the light part of the pump LED and the light part of the phosphor. This means that the relative intensity is massively lower in this wavelength range compared with the rest of the spectrum (see FIG. 20). A second problem is the fact that the center wavelength of the pump LED is subjected to a large copy scattering. The manufacturer of the light-emitting diodes therefore often measures every individual light-emitting diode produced and then sorts them on the basis of certain criteria, for example depending on the position of the center wavelength of the light of the pump LED. It should be noted that, unlike the light of the semiconductor, the light of the phosphor is subjected to practically no copy scattering as far as the position of the spectrum is concerned.

In color measuring technology, the spectrum in the range of 400 nm to 700 nm is important. In order to achieve good measuring accuracy, sufficient light must be available everywhere, at least in this range. Against this background, two difficulties arise with regard to the measuring technique in connection with the above-mentioned problems. If the center wavelength of the blue pump LED lies more in the short wavelength (e.g. at 430 nm), there is still sufficient light, even at 400 nm, but the depression in the spectrum (between semiconductor light and phosphor light) is more pronounced due to the spectrally unchanged position of the phosphor light and there is therefore little light in this range (ca. between 450 nm and 500 nm). If, on the other hand, the center wavelength of the pump LED is shifted more towards the longer wavelength, although this depression is essentially less pronounced there is no longer much light available at short wavelengths, in particular between 400 nm and 430 nm. In such a situation, the densitometric density of the process color yellow, for example, can no longer be meaningfully determined. These two situations may be seen in the two spectrum groups SPG1 and SPG2 in FIG. 20.

These problems can be solved by another underlying principle of the invention in the following manner. The available light-emitting diodes are divided into two groups by sorting them on the basis of their emission spectra corresponding to the spectrum groups SPG1 and SPG2 of FIG. 20. One group has the center wavelength of the pump LED closer to the shorter wavelengths (e.g. at 430 nm) and the other has those closer towards the longer wavelengths (e.g. at 450 nm). The light-emitting diodes of the two groups can now be assembled to form a lighting system whereby light-emitting diodes can be selected from one or the other group for the color channels depending on color filter so that the above-mentioned problems do not occur. This means, for example, that light-emitting diodes for the color filter with the center wavelength at 420 nm can be selected from one group and light-emitting diodes from the other group can be used for the color filter with a center wavelength at 470 nm, for example. The same approach may also be used with more groups more finely sub-divided.

As a result of another important aspect of the invention, the measuring device MD may contain another spectral measuring head in addition to the line sensors for taking spectral measurements of individual image elements, as schematically indicated in FIG. 21. This spectral measuring head 300 can be moved in the y direction by means of a motorized drive, schematically indicated by arrow A4 in the drawing, separately from the other components of the measuring device and hence in the x direction in conjunction with the movement of the measuring carriage MC and positioned above any image element of the measurement object. The spectral measuring head 300 and its drive in the y direction are naturally also controlled by the measuring and control system MDC. The spectral measuring head 300 is preferably equipped with a polarization filter 301, which can be introduced into the measurement optical path and moved back out of it again by remote control so that spectral measurements can be taken selectively with and without the polarization filter. The movement of the polarization filter 301 is symbolized by arrow A5 in FIG. 21. The polarization filter 301 comprises two concentric parts, the polarization directions of which intersect one another. The lighting optical path extends through the outer part, whilst the measuring light optical path extends through the inner part. To enable measurements to be taken with different filters at the same time, it is also possible to provide more than one independent spectral measuring head, for example in order to obtain measurements with two spectral measuring heads with and without a polarization filter.

In practical application, the spectral measuring head 300 is used for high-precision (spectral) measurements on relatively few selected image elements of the measurement object S. It is typically used to measure the color control strip CMS (FIG. 1) provided as standard on printed sheets. This may be done in a separate scanning pass or alternatively together with the or one of the scanning passes of the measuring device MD. In both situations, in view of the fact that the exact position of selected image elements is not known a priori, it is of particular advantage if the image data detected by the measuring device with the line sensors is interpreted so that they can be used for positioning the independent spectral measuring head on specific image elements. For example, the exact position of the color control strip CMS can be determined during the measuring operation in particular and as a result, the independent spectral measuring head can be selectively positioned above the relevant image elements.

In terms of quality, the spectral measuring head is a highly precise color measuring system. It satisfies all the demands placed on measuring technology as set out in international standards governing color measuring technology (for example ISO 13655 or DIN 5033). More particularly, the individual spectral measuring head 300 is designed with an annular or circular measuring geometry so that it is not sensitive to the effects of direction when the test sample is rotated underneath the spectral individual measuring head. An example of such a spectral measuring head is the spectral photometer, SpectroEye, made by GretagMacbeth AG, which can be used as a spectral measuring head in the measuring device. It is also of advantage if the spectral measuring head and the image measuring unit have a lighting spectrum in the measuring light without an ultra-violet (UV) element. This characteristic can be achieved by using an edge filter in the optical light system, which suppresses the spectral element in the lighting spectrum below the wavelength of 400 nm. Commercially available absorption filter glasses made by the Schott company, for example, may be used for such filters. Suppressing the UV element makes it easier to correct the measurement data because allowance does not have to be made for the non-linear effects for the different energization of optical brighteners in the substrate. If UV suppression is not used, compensation must be made for the fluorescence effects of the optical brighteners in the correction model. Ideally, allowance is made for this compensation in a correction model when making allowance for the effect of the measuring geometry and type of medium.

A particularly practical embodiment of the measuring device and scanning device proposed by the invention will be explained below with reference to FIGS. 22-25. The general construction with the measuring table MT and measuring carriage MC is the same as that described above and it is only the measuring device MD disposed in the measuring carriage which is different. Accordingly, the description will concentrate on the latter.

Figure 22:
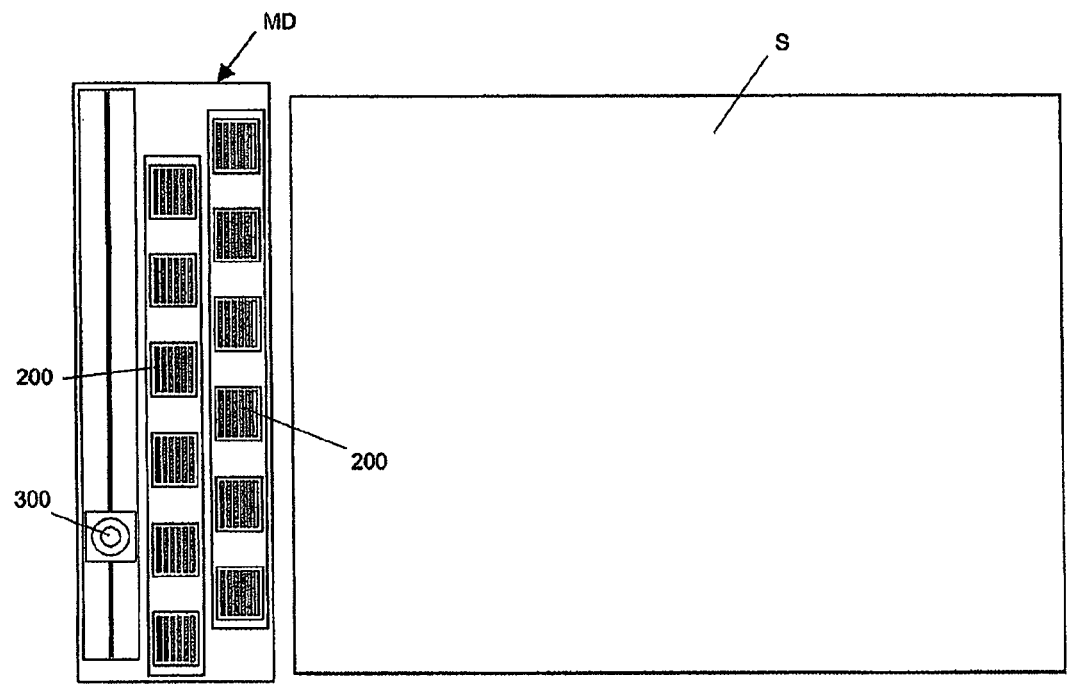
FIG. 22 shows another example of a particularly preferred embodiment of the scanning device proposed by the invention with an additional spectral measuring head.

FIG. 22 is a very symbolic diagram of a measuring device MD in the measuring carriage MC sub-divided into a larger number of measuring modules 200 and also incorporating a spectral measuring head 300, in a position adjacent to the measurement object S. The measuring carriage guides the measuring device MD, as described above, in a first pass from left to right (in the drawing) above the measurement object S (outward movement) and then immediately in a second pass from right to left back to the initial position (return movement).

Figure 23:
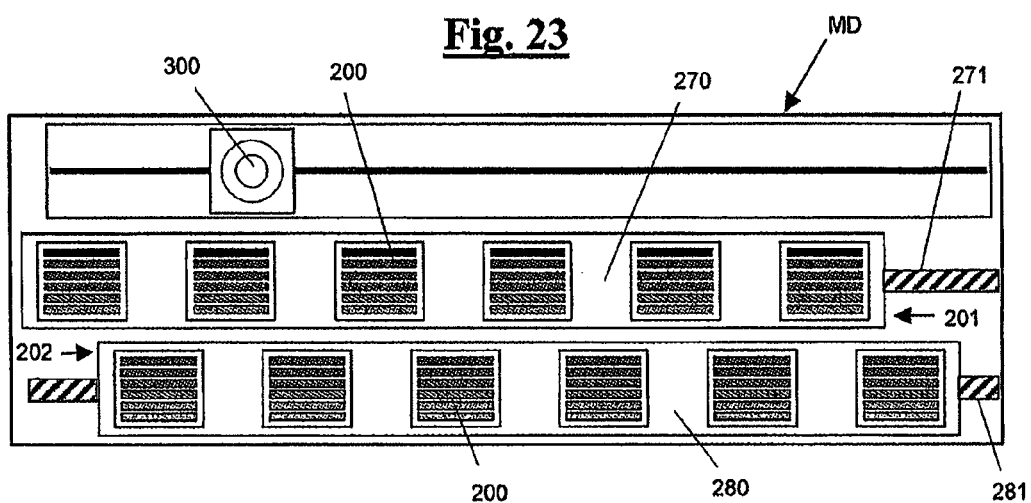
FIG. 23 illustrates the measuring device of the scanning device illustrated in FIG. 22 with the measuring module groups contained in it in a first movement position.
Figure 24:
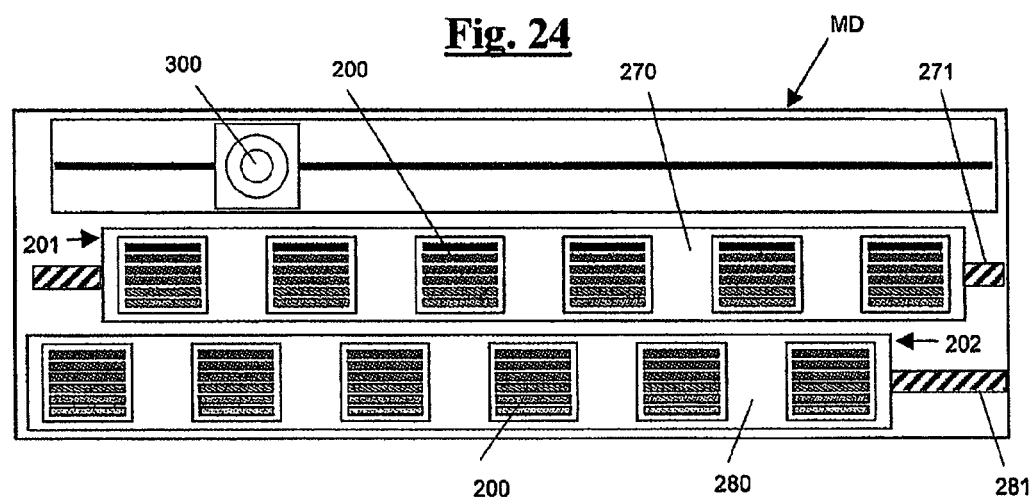
FIG. 24 illustrates the measuring device of the scanning device shown in FIG. 22 with the measuring module groups contained in it in a second movement position.

As may be seen in slightly more detail from FIGS. 23 and 24, the measuring modules 200 are disposed in two groups 201 and 202, as was the case in FIG. 11, and the measuring modules of one group and those of the other group stand on a gap and thus slightly overlap with one another (in the y direction) so that overall, no gaps occur in the scan. The measuring modules 200 are of identical designs, as explained in connection with the measuring modules illustrated in FIGS. 13-19. All the measuring modules 200 are identical with the exception of the color filter used. All the measuring modules within a group contain the same set of color filters but the color filter sets of one group is different from that of the other group. In the example illustrated, every measuring module 200 is equipped with 6 filters, thereby resulting in a total maximum of 12 different color channels.

The measuring modules 200 of each group 201 and 202 are each mounted on a carriage 270 respectively 280 so that they can not move relative to one another. The two module groups 201 and 202 as a whole can be moved by conventional drive means, although these are not illustrated in detail, in the longitudinal direction of the measuring carriages in opposite directions by half the distance between two adjacent modules. The drive means might be two motor driven spindles 271 and 281, for example, which are in turn controlled by the measurement and drive control system MDC. As may be seen from the diagram in section shown in FIG. 25, the carriages 270 and 280 are advantageously provided in the form of cooling elements for dispelling heat from the module housings 210.

FIG. 23 illustrates the two module groups 201 and 202 in the initial position, whilst FIG. 24 shows them in the moved position. As illustrated, when the module groups are in the moved position, the positions of the modules 200 in the two groups are reversed. As the module groups are moved outwards by the measuring device MD from the initial position and as they are moved back from the moved position, every point of the image of the measurement object is fully scanned in all the existing color channels.

Figure 25:
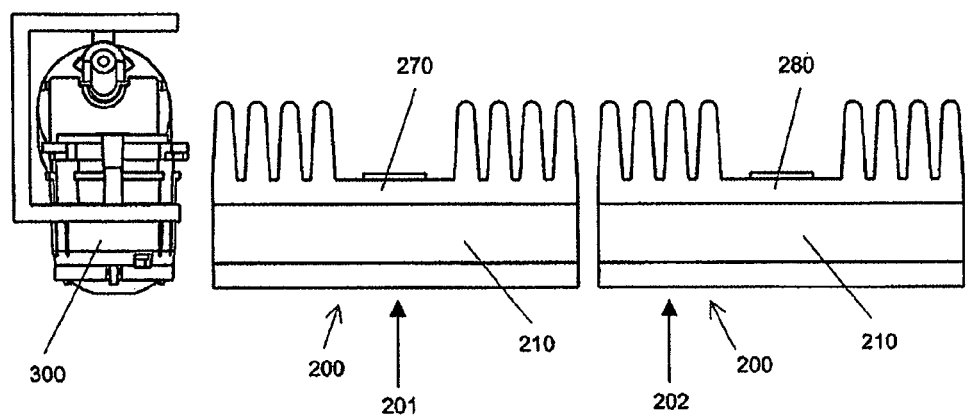
FIG. 25 shows a vertical section (parallel with the y-z co-ordinate plane) through the measuring device illustrated in FIG. 21.

FIG. 25 shows the two module groups 401 and 402 in section, parallel with the x-z-co-ordinate plane, and the additional spectral measuring head 300.

Figure 1:
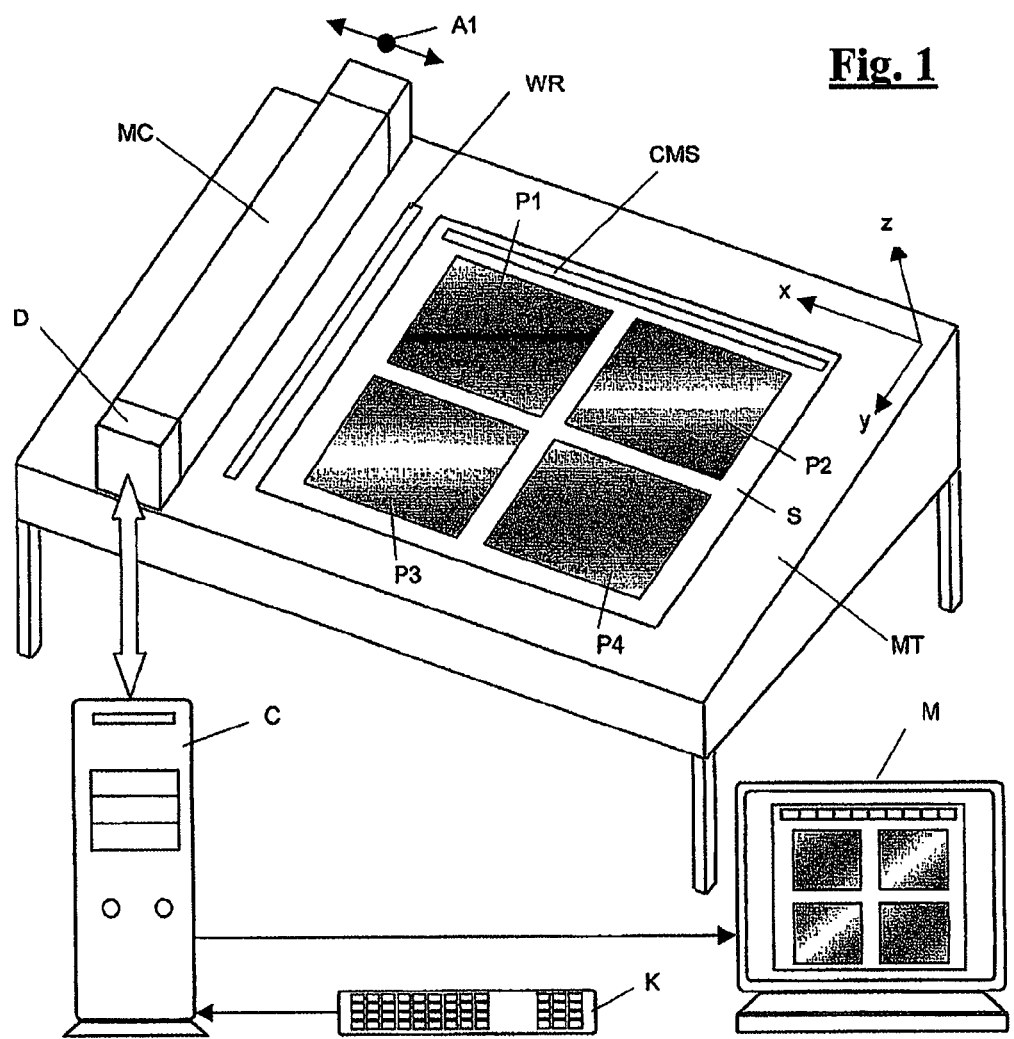
FIG. 1 shows a simplified overall view of an example of an embodiment of the scanning device proposed by the invention.

As a matter of principle in offset printing, the color control strip CMS is always disposed along a specific side of the printed sheet (in FIG. 1 along the long side, in other words in the x direction). When the measuring carriage MC and hence the measuring device MD contained in it is disposed parallel with the color control strip CMS, it is possible to scan the usually narrow color control strip with only a very small movement of the measuring carriage MC and hence within a very short time. The height of a color control strip typically accounts for only 1% of the height of a printed sheet (see FIG. 1 for more details), and the color control strip alone can therefore usually be read 100 times faster than the sheet as a whole. When scanning a sheet, if the color control strip alone is scanned first and then the whole sheet, a zone-dependent rule recommendation can be transmitted to the printing machine control system within a very short time in the case of electronically controlled printing machines. Printing orders can therefore be handled much quicker and with less waste paper.

Sufficiently accurate color values X,Y,Z can be calculated from the scanning values obtained from the multi-channel measuring device MD for every image element on the basis of the following matrix transform. In the situation where there are 6 color channels, the transform matrix with the associated 6 scanning values $M_1 \ldots M_6$ looks as follows:

$$\begin{pmatrix} X \\ Y \\ Z \end{pmatrix} = \begin{pmatrix} k_{11} & k_{12} & k_{13} & k_{14} & k_{15} & k_{16} \\ k_{21} & k_{22} & k_{23} & k_{24} & k_{25} & k_{26} \\ k_{31} & k_{32} & k_{33} & k_{34} & k_{35} & k_{36} \end{pmatrix} \cdot \begin{pmatrix} M_1 \\ M_2 \\ M_3 \\ M_4 \\ M_5 \\ M_6 \end{pmatrix}$$

The coefficients $k_{11} \ldots k_{36}$ of the transform matrix can be determined empirically using a larger number of comparative measurements (once with the measuring device proposed by the invention and once with a precision spectral measuring device). This approach is naturally not restricted to six color channels but the results are less precise with a smaller number of color channels. Instead of using an external spectral measuring device, it would also be possible to use the spectral measuring head 300 mentioned above.

Determining the coefficients of the transform matrix by means of a compensating calculation enables production errors and tolerances for the different filters as well as the light-emitting diodes to be corrected. An individual transform matrix must therefore be calculated for every spatial area of the measuring device corresponding to a unit comprising light-emitting diodes and filters.

The CIE color values X,Y,Z are determined on the basis of a known definition (CIE Publication 15.2) for a combination of lighting type and normal observer. Specific transform matrices may therefore be run for every combination of lighting type and normal observer.

With a reduced set of 6-8 different color filters, the accuracy of the color density measurement can also be improved by using a similar transform matrix. The transform for 6 filters is set out in the equation below:

$$\begin{pmatrix} Dc \\ Dm \\ Dy \end{pmatrix} = \begin{pmatrix} k_{11} & k_{12} & k_{13} & k_{14} & k_{15} & k_{16} \\ k_{21} & k_{22} & k_{23} & k_{24} & k_{25} & k_{26} \\ k_{31} & k_{32} & k_{33} & k_{34} & k_{35} & k_{36} \end{pmatrix} \cdot \begin{pmatrix} D_1 \\ D_2 \\ D_3 \\ D_4 \\ D_5 \\ D_6 \end{pmatrix}$$

$D_1 \ldots D_6$ are the density values of the individual scanning measurement values $M_1 \ldots M_6$. Dc, Dm, Dy are density values based on a specific density standard from ISO standard 5. With a reduced filter set (few color channels), it is of advantage to choose a density standard with broadband filter functions with half-widths in the range of from 30 to 50 nm, such as Status E for example, as the density reference.

The coefficients $k_{11} \ldots k_{36}$ of the transform matrix may be determined empirically using a larger number of comparative measurements of the corresponding density values (once with the multi-channel line scan and once with a precision spectral measuring device). Instead of an external spectral measuring device, it would again also be possible to use the spectral measuring head 300 mentioned above.

Figure 26:
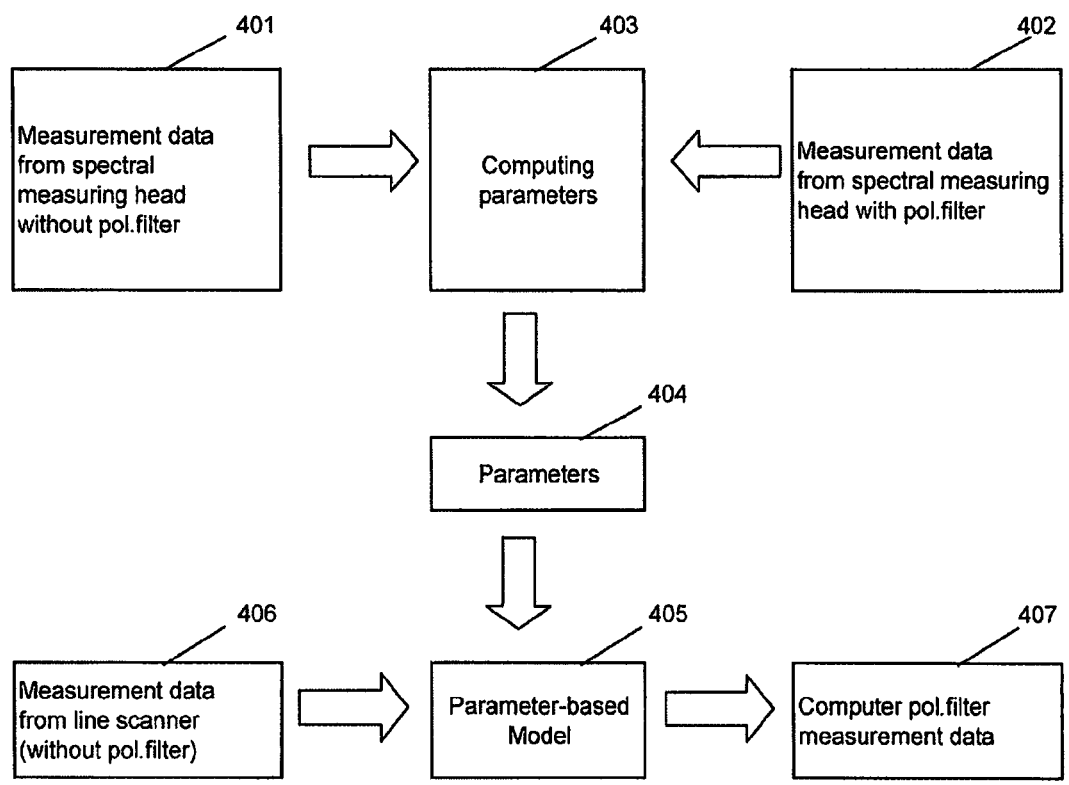
FIG. 26 is a block diagram illustrating the computation used to convert the measurement values.

It is difficult to use polarization filters in the measuring device MD with the line sensors for various reasons, e.g. because the measurement light is damped to too high a degree as a result. In many applications, however, it might be necessary or at least conducive to take measurements with polarization filters. By virtue of another aspect of the invention, pole filter scanning values are calculated from the scanning values generated by the multi-channel measuring device MD without polarization filters, which correspond to a scan using polarization filters. This conversion is run in the external computer C, for example, using a model based on parameters, the parameters of which are determined from spectral scanning values measured using the spectral measuring head 300 at selected image elements with and without polarization filters 301. The selected image elements used are typically those of the color measuring strip CMS in the measurement object S. FIG. 26 illustrates these correlations. From the measurement data 401 respectively 402 obtained by the spectral measuring head 300 with and without polarization filters, parameters 404 are determined for the model in a parameter calculation stage 403 and incorporated in the model 405. It then converts the measurement data 406 from the line sensors obtained without polarization filters into corresponding pole filter measurement data 407. The correction model typically comprises an offset correction, a spectral scaling if necessary and a spectral independent multiplicative characteristic curve correction.

The parameters 404 are calculated by means of a compensation calculation which contains the correction model and the reference measurement values (spectral scanning values) measured with the spectral measuring head with and without polarization filters at the selected image elements are used as input variables and the correction parameters as variables. The compensation calculation is therefore run and the correction parameters calculated so that the reference values measured without polarization filters and then corrected using the correction model deviate as little as possible from the reference measurement values of the spectral measuring head measured with polarization filters.

The polarization filter correction or conversion into polarization filter image measurement values may also be implemented without using a separate spectral measuring head. In this case, the printed sheet is measured completely with the measuring device MD without polarization filters. Polarization filters in the measuring device MD are then pivoted into the lighting and collection channel and only a part area of the image is measured in a separate special scanning pass at a scanning speed approximately 10 times slower with polarization filters. This part area advantageously contains the color control strip CMS. The slower scanning speed means that the approximately 10 times longer measuring times (integration times) needed when using polarization filters due to the loss of light can be achieved. The conversion parameters are determined and the measurement values are converted by analog using the methods explained in connection with FIG. 26 but instead of using the measurement values 401 and 402 determined by the spectral measuring head, the measurement values originating from the selected part area of the image measured by the measuring device MD with and without polarization filters are used. FIG. 3 symbolically illustrates a polarization filter, denoted by reference 18, comprising two parts with crossed polarization directions. Arrow 18a symbolizes the ability to move into the optical paths and out of the optical paths.

For special applications, it is of interest to know the corresponding reflectance spectrum for every image pixel. If the image data is detected with only a reduced scanning set (few color channels), approximated spectra can be generated from the scanning values using algorithms from the spectral Color Management. These techniques are explained at length in the dissertation "Navigating the roadblocks to spectral color reproduction: Data-efficient multichannel spectral imaging and spectral color management" by Mitchell R. Rosen, Rochester Institute of Technology, August 2004.

Spectral image data can also be determined from the scanning values measured by the measuring device MD with multiple channels in the manner outlined below using the spectral measuring head 300. The color control strip is spectrally measured with the spectral measuring head 300. The color control strip CMS contains control fields (full tone color fields and halftone printed fields) for all the colors involved in the printing process. Precise reflectance spectra exist for these fields once they have been measured with the spectral measuring head. These reflectance spectra of the CMS form the basis for calculating the reflectance spectra from the (multichannel scanned) scanning values. It is known that the spectrum for any image pixel can be described with a model using the spectra of the full tones and some of the halftone fields, if the halftone values of the color structure for the image data are known. A print model is usually based on Neugebauer's theory for describing the halftone printing process and the theories of Kubelka Munk or Hoffmann Schmelzer for the simulation of full tone test samples. The image data is defined by a relatively small number of scanning values. Since the effectively measured image measurement values are known, the accuracy of the spectra calculation can be improved with the print model. The print model describes the spectrum in every image pixel as a weighted combination of the base spectra. These base spectra can also be parameterized as a function of the scanning values of image measurement technology. This function is defined by means of a compensation calculation with the measurement values of the color control strip CMS which were determined with the two measuring devices (line scanner and spectral measuring head).

The measuring device respectively scanning device proposed by the invention enable whole printed sheets to be scanned at high speed and is not very complex in terms of its design. It combines the advantages of the technologies of known imaging devices but without their inherent disadvantages. It is therefore suitable for quality control applications in the graphics industry and for colorimetric control of printing processes.

The invention claimed is:

1. A measuring device for photoelectrically measuring a measurement object on the basis of image elements, comprising:
   (a) a measuring unit that is adapted to simultaneously photoelectrically scan a plurality of image elements of a measurement object disposed in a line and generate associated measurement signals for every scanned image element,
   (b) a lighting system for applying illuminating light to the image element of the measurement object,
   (c) a wavelength range-selective photoelectric receiver unit, and
   (d) optical pick-up means which pick up the measurement light reflected by the illuminated image elements of the measurement object and direct it to the photoelectric receiver unit,
   wherein the photoelectric receiver unit converts the measurement light directed to it from the image elements of the measurement object into corresponding measurement signals for the image elements of the measurement object,
   wherein the lighting system has a plurality of parallel linear-shaped arrays of light-emitting diodes which apply illuminating light to the measurement object in a number of parallel illuminating strips,
   wherein the lighting system has means for limiting the angle of incidence range so that essentially every image element disposed in the illuminating strip and illuminated receives light at an angle of incidence range standardized for color measuring applications,
   wherein the photoelectric receiver unit has a number of parallel photoelectric line sensors disposed at a distance apart corresponding to the number of illuminating strips which are oriented parallel with the longitudinal extension of the illuminating strips and are sensitized to different wavelength ranges by color filters connected upstream,
   wherein the optical pick-up means has a number of linear optical arrays corresponding to the number of line sensors which are each oriented parallel with the illuminating strips and direct measurement light reflected from an image line within the illuminating strips onto one of the respective line sensors, and the linear optical arrays are configured so that the measurement light from essentially every image element of the image lines is picked up at only an angle of reflection range for standard color measuring applications, and
   wherein the illuminating strips with the associated linear optical arrays and line sensors are optically screened from one another so that measurement signals from image lines in adjacent illuminating strips do not mutually affect one another.

2. Measuring device according to claim 1, wherein means are provided which at least reduce the mutual effect of the measurement signals from adjacent image elements within the same image lines of the measurement object.

3. Measuring device according to claim 1, wherein the means for limiting the angle of incidence range of the linear-shaped arrays of light-emitting diodes comprise associated collimator lenses.

4. Measuring device according to claim 1, wherein screening plates are disposed between the individual light-emitting diodes of a linear light-emitting diode array in order to limit the angle of illumination in the direction of the line.

5. Measuring device according to claim 1, wherein the means for limiting the angle of incidence range comprise a slot diaphragm, which limits the width of the illuminated illuminating strips on the measurement object.

6. Measuring device according to claim 1, wherein, in order to reduce cross-talk effects within the image lines, the color filters are positioned at an angle to the main optical path of the measurement light hitting the line sensors.

7. Measuring device according to claim 1, wherein the linear optical arrays comprise parallel rows of aligned gradient index lenses.

8. Measuring device according to claim 1, wherein the line sensors are provided in the form of integrated CIS (contact image sensor) elements.

9. Measuring device according to claim 1, wherein the linear arrays of light-emitting diodes comprise high-performance light-emitting diodes with a Lambert emission characteristic.

10. Measuring device according to claim 1, wherein at least six line sensors and associated linear optical arrays are provided, and the line sensors are sensitized to different wavelength ranges by means of color filters connected upstream.

11. Measuring device according to claim 10, wherein three of the color filters have the bandpass characteristic of filters standardized for color density measurements and three of the color filters have different bandpass characteristics optimized for color measurements.

12. Measuring device according to claim 1, wherein each pair of adjacent illuminating strips is illuminated by a common linear array of light-emitting diodes.

13. Measuring device according to claim 1, wherein the spectral characteristics of the light-emitting diodes of the linear arrays are adapted to the bandpass characteristics of the color filters used.

14. Measuring device according to claim 1, wherein at least one of the linear arrays comprises light-emitting diodes emitting in the near infrared range.

15. Measuring device according to claim 1, wherein at least one of the line sensors is sensitized to two different wavelength ranges, one of which lies in the near infrared range.

16. Measuring device according to claim 1, wherein at least one of the linear arrays of light-emitting diodes comprises selectively activatable light-emitting diodes with a different spectral characteristic and at least one of the color filters is provided in the form of a double bandpass filter which transmits two different wavelength ranges and is adapted to the different spectral characteristics of the light-emitting diodes.

17. Measuring device according to claim 1, further comprising at least one spectral measuring head which can be moved by motor parallel with the illuminating strips for taking spectral measurements of individual image elements.

18. Measuring device according to claim 17, wherein the spectral measuring head is equipped with a polarization filter which is movable into and back out of the measurement optical path so that spectral measurements are taken with and without polarization filters.

19. Measuring device according to claim 1, wherein a modular construction is employed and comprises a number of measuring modules of essentially identical design, each of which contains separate linear arrays of light-emitting diodes, separate linear optical arrays and separate line sensors which are sensitized to different wavelength ranges by color filters connected upstream.

20. Measuring device according to claim 19, wherein the measuring modules are disposed in lines spaced at a mutual distance apart in two parallel module groups, and the measuring modules of one group stand on a gap with respect to the measuring modules of the other group and preferably slightly overlap in the longitudinal direction.

21. Measuring device according to claim 20, wherein the two module groups are driven so that they can be moved in the longitudinal direction in opposite directions, and the lengthways positions of the measuring modules of one module group can be swapped for the lengthways positions of the measuring modules of the other module group.

22. Measuring device according to claim 21, wherein at least some of the measuring modules of one module group are equipped with different color filters from the measuring modules of the other module group.

23. Measuring device according to claim 19, wherein the measuring modules are each configured for six wavelength ranges.

24. Measuring device according to claim 1, wherein the measuring unit is equipped with polarization filters which are movable out of the optical paths, and computing means are provided which convert the measurement values generated by the line sensors without using a polarization filter into polarization filter measurement values using a parameter-based model and measurement values detected by the line sensors in only selected image elements with and without polarization filters.

25. Measuring device according to claim 18, wherein computing means are provided which convert the measurement values generated by the line sensors without using a polarization filter into polarization filter measurement values using a parameter-based model and measurement values detected by the spectral measuring head in selected image elements with and without polarization filters.

26. Measuring device according to claim 1, wherein computing means are provided which convert the measurement values generated by the line sensors into color values or color density values conforming to standard using a model or transform.

27. Measuring device according to claim 17, wherein computing means are provided which convert the measurement values generated by the line sensors into spectral measurement values using a parameter-based model, and the parameters of the model are determined from measurement values generated in selected image elements both by means of the line sensors and by means of the spectral measuring head.

28. Measuring device according to claim 1, wherein computing means are provided which run a computed scattered light correction on the basis of measurements on a test sample.

29. Scanning device for photoelectrically measuring a measurement object on the basis of image elements, comprising:
 (a) a measuring table to which the measurement object can be secured for the measurement,
 (b) a measuring device which is movable above the surface of the measuring table which simultaneously photoelectrically scans a plurality of image elements respectively lying in a line of the measurement object secured to the measuring table and generates an associated measurement signal for every scanned image element,
 (c) a drive system which moves the measuring device above the measurement object so that all the image elements of the measurement object are detectable,
 (d) a measurement and drive control system for the measuring device and the drive system, and
 (e) a processing unit for processing and evaluating the measurement signals scanned by the measuring device from the scanned image elements of the measurement object,
 wherein the measuring device is equipped with a lighting system for applying illuminating light to the image elements of the measurement object, with a wavelength range-selective photoelectric receiver unit and with pick-up means, which pick-up means pick up measurement light reflected by illuminated image elements of the measurement objects and direct it to the photoelectric receiver unit, and the photoelectric receiver unit converts the measurement light from the image elements of the measurement object directed to it into corresponding measurement signals for the image elements of the measurement object,
 wherein the lighting system comprises several parallel linear arrays of light-emitting diodes which apply illuminating light to the measurement object parallel illuminating strips, and the lighting system has means for limiting the angle of incidence range so that essentially every image element disposed in the illuminating strips and illuminated receives light only at an angle of incidence range standardized for color measuring applications, and
 wherein the photoelectric receiver unit comprises a number of parallel photoelectric line sensors corresponding to the number of illuminating strips which are oriented parallel with the longitudinal extension of the illuminating strips and are sensitized to different wavelength ranges by color filters connected upstream, and
 wherein the optical pick-up means comprise a number of linear optical arrays corresponding to the number of line sensors which are oriented parallel with the illuminating strips and direct measurement light reflected from a respective image line within the illuminating strips onto a respective one of the line sensors, and
 wherein the linear optical arrays are configured so that the measurement light from essentially every image element of the image lines is picked up only at an angle of reflection range standardized for color measuring applications, and
 wherein the illuminating strips with the associated linear optical arrays and line sensors are optically mutually screened off from one another so that measurement signals from image lines in adjacent illuminating strips do not mutually affect one another.

30. Scanning device according to claim 29, wherein the measurement object is a printed sheet that is printed in multiple colors.

31. Scanning device according to claim 29, wherein the length of the measuring device is shorter than the maximum scanning region of the measuring table to be passed over, and the measurement and drive control system is designed so that the entire measurement object is scanned in two or more scanning passes and the measuring device is moved in the longitudinal direction for every scanning pass.

32. Scanning device according to claim 29, wherein the measurement and drive control system is designed to scan only selected image elements of the measurement object, in a scanning operation at a lower scanning speed so that sufficiently long measuring times are available during this first scanning operation for the use of polarization filters.

33. Scanning device according to claim 29, wherein the measuring device is of a modular construction and comprises a number of measuring modules of essentially identical design, each of which contains separate linear arrays of light-emitting diodes, separate linear optical arrays and separate line sensors sensitized to different wavelength ranges by color filters connected upstream, wherein three of the color filters in all of the measuring modules are identical so that all the measuring modules scan the image elements of the measurement object in the same three wavelength ranges, and computing means are provided which compute a preview image from the scanning values of the image elements in these three wavelength ranges and preferably display it on a color monitor.

* * * * *